United States Patent [19]
Rozen et al.

[11] Patent Number: 6,074,821
[45] Date of Patent: Jun. 13, 2000

[54] CDNA FOR HUMAN METHYLENETETRAHYDROFOLATE REDUCTASE

[75] Inventors: Rima Rozen; Philippe Goyette, both of Québec, Canada

[73] Assignee: McGill University, Montreal, Canada

[21] Appl. No.: 08/738,000

[22] PCT Filed: May 25, 1995

[86] PCT No.: PCT/CA95/00314

§ 371 Date: Feb. 12, 1997

§ 102(e) Date: Feb. 12, 1997

[87] PCT Pub. No.: WO95/33054

PCT Pub. Date: Dec. 7, 1995

[30] Foreign Application Priority Data

May 26, 1994 [GB] United Kingdom .................. 9410620

[51] Int. Cl.[7] .............................. C12Q 1/68; C12P 19/34; C07H 21/04

[52] U.S. Cl. ........................... 435/6; 435/91.2; 536/23.5; 536/24.31; 536/24.33

[58] Field of Search ..................... 435/6, 91.2; 536/23.5, 536/24.31, 24.33

[56] References Cited

PUBLICATIONS

Goyette P et al., *Nature Genetics*, 1994, 7:195–200.
Goyette P et al., *Am, J. Hum. Genet.*, 1995, 56:1052–1059.
Frosst P et al., *Nature Genetics*, 1995, 10:111–113.
Orita, M. et al., *Genomics*, 1989, 5:8874–8879.
Engbersen et al., *Am. J. Hum. Genet.*, 1995, 56:142–150.
Stauffer et al. Molecular Gen Genetics. 212: 246–251, 1988.

*Primary Examiner*—Carla J. Myers
*Attorney, Agent, or Firm*—Clark & Elbing LLP

[57] ABSTRACT

The present invention relates to a cDNA probe for human methylenetetrahydrofolate reductase (MTHFR), and its uses. The probe of the present invention may be used for the identification of sequence abnormalities in patients with severe or mild MTHFR deficiency, including cardiovascular patients and patients with neurologic symptoms. A human MTHFR protein which hybridizes to the probe of the present invention may be used for therapy of MTHFR-deficiency patients by biochemical or pharmacological approaches.

7 Claims, 18 Drawing Sheets

```
         10        20        30        40        50
    x    x    x    x    x    x    x    x    x    x
AAT TCC GGA GCC ATG GTG AAC GAA GCC AGA GGA AAC AGC AGC CTC AAC CCC
TTA AGG CCT CGG TAC CAC TTG CTT CGG TCT CCT TTG TCG TCG GAG TTG GGG
Asn Ser Gly Ala Met Val Asn Glu Ala Arg Gly Asn Ser Ser Leu Asn Pro›

60        70        80        90       100
    x    x    x    x    x    x    x    x    x    x
TGC TTG GAG GGC AGT GCC AGC AGT GGC AGT GAG AGC TCC AAA GAT AGT TCG
ACG AAC CTC CCG TCA CGG TCG TCA CCG TCA CTC TCG AGG TTT CTA TCA AGC
Cys Leu Glu Gly Ser Ala Ser Ser Gly Ser Glu Ser Ser Lys Asp Ser Ser›

110       120       130       140       150
    x    x    x    x    x    x    x    x    x    x
AGA TGT TCC ACC CCG GGC CTG GAC CCT GAG CGG CAT GAG AGA CTC CGG GAG
TCT ACA AGG TGG GGC CCG GAC CTG GGA CTC GCC GTA CTC TCT GAG GCC CTC
Arg Cys Ser Thr Pro Gly Leu Asp Pro Glu Arg His Glu Arg Leu Arg Glu›

160       170       180       190       200
    x    x    x    x    x    x    x    x    x    x
AAG ATG AGG CGG CGA TTG GAA TCT GGT GAC AAG TGG TTC TCC CTG GAA TTC
TTC TAC TCC GCC GCT AAC CTT AGA CCA CTG TTC ACC AAG AGG GAC CTT AAG
Lys Met Arg Arg Arg Leu Glu Ser Gly Asp Lys Trp Phe Ser Leu Glu Phe›

210       220       230       240       250
    x    x    x    x    x    x    x    x    x    x
TTC CCT CCT CGA ACT GCT GAG GGA GCT GTC AAT CTC ATC TCA AGG TTT GAC
AAG GGA GGA GCT TGA CGA CTC CCT CGA CAG TTA GAG TAG AGT TCC AAA CTG
Phe Pro Pro Arg Thr Ala Glu Gly Ala Val Asn Leu Ile Ser Arg Phe Asp›

260       270       280       290       300
    x    x    x    x    x    x    x    x    x    x
CGG ATG GCA GCA GGT GGC CCC CTC TAC ATA GAC GTG ACC TGG CAC CCA GCA
GCC TAC CGT CGT CCA CCG GGG GAG ATG TAT CTG CAC TGG ACC GTG GGT CGT
Arg Met Ala Ala Gly Gly Pro Leu Tyr Ile Asp Val Thr Trp His Pro Ala›

310       320       330       340       350
    x    x    x    x    x    x    x    x    x    x
GGT GAC CCT GGC TCA GAC AAG GAG ACC TCC TCC ATG ATG ATC GCC AGC ACC
CCA CTG GGA CCG AGT CTG TTC CTC TGG AGG AGG TAC TAC TAG CGG TCG TGG
Gly Asp Pro Gly Ser Asp Lys Glu Thr Ser Ser Met Met Ile Ala Ser Thr›
```

FIG. 1A

```
       360         370         380         390         400
  x     x     x     x     x     x     x     x     x     x
GCC   GTG   AAC   TAC   TGT   GGC   CTG   GAG   ACC   ATC   CTG   CAC   ATG   ACC   TGC   TGC   CGT
CGG   CAC   TTG   ATG   ACA   CCG   GAC   CTC   TGG   TAG   GAC   GTG   TAC   TGG   ACG   ACG   GCA
Ala   Val   Asn   Tyr   Cys   Gly   Leu   Glu   Thr   Ile   Leu   His   Met   Thr   Cys   Cys   Arg›

410         420         430         440         450
  x     x     x     x     x     x     x     x     x     x
CAG   CGC   CTG   GAG   GAG   ATC   ACG   GGC   CAT   CTG   CAC   AAA   GCT   AAG   CAG   CTG   GGC
GTC   GCG   GAC   CTC   CTC   TAG   TGC   CCG   GTA   GAC   GTG   TTT   CGA   TTC   GTC   GAC   CCG
Gln   Arg   Leu   Glu   Glu   Ile   Thr   Gly   His   Leu   His   Lys   Ala   Lys   Gln   Leu   Gly›

460         470         480         490         500         510
  x     x     x     x     x     x     x     x     x     x
CTG   AAG   AAC   ATC   ATG   GCG   CTG   CGG   GGA   GAC   CCA   ATA   GGT   GAC   CAG   TGG   GAA
GAC   TTC   TTG   TAG   TAC   CGC   GAC   GCC   CCT   CTG   GGT   TAT   CCA   CTG   GTC   ACC   CTT
Leu   Lys   Asn   Ile   Met   Ala   Leu   Arg   Gly   Asp   Pro   Ile   Gly   Asp   Gln   Trp   Glu›

520         530         540         550         560
  x     x     x     x     x     x     x     x     x     x
GAG   GAG   GAG   GGA   GGC   TTC   AAC   TAC   GCA   GTG   GAC   CTG   GTG   AAG   CAC   ATC   CGA
CTC   CTC   CTC   CCT   CCG   AAG   TTG   ATG   CGT   CAC   CTG   GAC   CAC   TTC   GTG   TAG   GCT
Glu   Glu   Glu   Gly   Gly   Phe   Asn   Tyr   Ala   Val   Asp   Leu   Val   Lys   His   Ile   Arg›

570         580         590         600         610
  x     x     x     x     x     x     x     x     x     x
AGT   GAG   TTT   GGT   GAC   TAC   TTT   GAC   ATC   TGT   GTG   GCA   GGT   TAC   CCC   AAA   GGC
TCA   CTC   AAA   CCA   CTG   ATG   AAA   CTG   TAG   ACA   CAC   CGT   CCA   ATG   GGG   TTT   CCG
Ser   Glu   Phe   Gly   Asp   Tyr   Phe   Asp   Ile   Cys   Val   Ala   Gly   Tyr   Pro   Lys   Gly›

620         630         640         650         660
  x     x     x     x     x     x     x     x     x     x
CAC   CCC   GAA   GCA   GGG   AGC   TTT   GAG   GCT   GAC   CTG   AAG   CAC   TTG   AAG   GAG   AAG
GTG   GGG   CTT   CGT   CCC   TCG   AAA   CTC   CGA   CTG   GAC   TTC   GTG   AAC   TTC   CTC   TTC
His   Pro   Glu   Ala   Gly   Ser   Phe   Glu   Ala   Asp   Leu   Lys   His   Leu   Lys   Glu   Lys›

670         680         690         700         710
  x     x     x     x     x     x     x     x     x     x
GTG   TCT   GCG   GGA   GCC   GAT   TTC   ATC   ATC   ACG   CAG   CTT   TTC   TTT   GAG   GCT   GAC
CAC   AGA   CGC   CCT   CGG   CTA   AAG   TAG   TAG   TGC   GTC   GAA   AAG   AAA   CTC   CGA   CTG
Val   Ser   Ala   Gly   Ala   Asp   Phe   Ile   Ile   Thr   Gln   Leu   Phe   Phe   Glu   Ala   Asp›
```

FIG. 1B

```
       720         730         740         750         760
  x     x     x     x     x     x     x     x     x     x
ACA   TTC   TTC   CGC   TTT   GTG   AAG   GCA   TGC   ACC   GAC   ATG   GGC   ATC   ACT   TGC   CCC
TGT   AAG   AAG   GCG   AAA   CAC   TTC   CGT   ACG   TGG   CTG   TAC   CCG   TAG   TGA   ACG   GGG
Thr   Phe   Phe   Arg   Phe   Val   Lys   Ala   Cys   Thr   Asp   Met   Gly   Ile   Thr   Cys   Pro›

770         780         790         800         810
  x     x     x     x     x     x     x     x     x     x
ATC   GTC   CCC   GGG   ATC   TTT   CCC   ATC   CAG   GGC   TAC   CAC   TCC   CTT   CGG   CAG   CTT
TAG   CAG   GGG   CCC   TAG   AAA   GGG   TAG   GTC   CCG   ATG   GTG   AGG   GAA   GCC   GTC   GAA
Ile   Val   Pro   Gly   Ile   Phe   Pro   Ile   Gln   Gly   Tyr   His   Ser   Leu   Arg   Gln   Leu›

820         830         840         850         860
  x     x     x     x     x     x     x     x     x     x
GTG   AAG   CTG   TCC   AAG   CTG   GAG   GTG   CCA   CAG   GAG   ATC   AAG   GAC   GTG   ATT   GAG
CAC   TTC   GAC   AGG   TTC   GAC   CTC   CAC   GGT   GTC   CTC   TAG   TTC   CTG   CAC   TAA   CTC
Val   Lys   Leu   Ser   Lys   Leu   Glu   Val   Pro   Gln   Glu   Ile   Lys   Asp   Val   Ile   Glu›

870         880         890         900         910
  x     x     x     x     x     x     x     x     x     x
CCA   ATC   AAA   GAC   AAC   GAT   GCT   GCC   ATC   CGC   AAC   TAT   GGC   ATC   GAG   CTG   GCC
GGT   TAG   TTT   CTG   TTG   CTA   CGA   CGG   TAG   GCG   TTG   ATA   CCG   TAG   CTC   GAC   CGG
Pro   Ile   Lys   Asp   Asn   Asp   Ala   Ala   Ile   Arg   Asn   Tyr   Gly   Ile   Glu   Leu   Ala›

920         930         940         950         960
  x     x     x     x     x     x     x     x     x     x
GTG   AGC   CTG   TGC   CAG   GAG   CTT   CTG   GCC   AGT   GGC   TTG   GTG   CCA   GGC   CTC   CAC
CAC   TCG   GAC   ACG   GTC   CTC   GAA   GAC   CGG   TCA   CCG   AAC   CAC   GGT   CCG   GAG   GTG
Val   Ser   Leu   Cys   Gln   Glu   Leu   Leu   Ala   Ser   Gly   Leu   Val   Pro   Gly   Leu   His›

970         980         990        1000        1010        1020
  x     x     x     x     x     x     x     x     x     x     x     x
TTC   TAC   ACC   CTC   AAC   CGC   GAG   ATG   GCT   ACC   ACA   GAG   GTG   CTG   AAG   CGC   CTG
AAG   ATG   TGG   GAG   TTG   GCG   CTC   TAC   CGA   TGG   TGT   CTC   CAC   GAC   TTC   GCG   GAC
Phe   Tyr   Thr   Leu   Asn   Arg   Glu   Met   Ala   Thr   Thr   Glu   Val   Leu   Lys   Arg   Leu›

1030        1040        1050        1060        1070
        x     x     x     x     x     x     x     x     x     x
      GGG   ATG   TGG   ACT   GAG   GAC   CCC   AGG   CGT   CCC   CTA   CCC   TGG   GCT   CTC   AGT   GCC
      CCC   TAC   ACC   TGA   CTC   CTG   GGG   TCC   GCA   GGG   GAT   GGG   ACC   CGA   GAG   TCA   CGG
      Gly   Met   Trp   Thr   Glu   Asp   Pro   Arg   Arg   Pro   Leu   Pro   Trp   Ala   Leu   Ser   Ala›
```

FIG. 1C

```
        1080            1090            1100            1110            1120
   x       x       x       x       x       x       x       x       x       x
 CAC CCC AAG CGC CGA GAG GAA GAT GTA CGT CCC ATC TTC TGG GCC TCC AGA
 GTG GGG TTC GCG GCT CTC CTT CTA CAT GCA GGG TAG AAG ACC CGG AGG TCT
 His Pro Lys Arg Arg Glu Glu Asp Val Arg Pro Ile Phe Trp Ala Ser Arg>

1130            1140            1150            1160            1170
   x       x       x       x       x       x       x       x       x       x
 CCA AAG AGT TAC ATC TAC CGT ACC CAG GAG TGG GAC GAG TTC CCT AAC GGC
 GGT TTC TCA ATG TAG ATG GCA TGG GTC CTC ACC CTG CTC AAG GGA TTG CCG
 Pro Lys Ser Tyr Ile Tyr Arg Thr Gln Glu Trp Asp Glu Phe Pro Asn Gly>

1180            1190            1200            1210            1220
   x       x       x       x       x       x       x       x       x       x
 CGC TGG GGC AAT TCC TCT TCC CCT GCC TTT GGG GAG CTG AAG GAC TAC TAC
 GCG ACC CCG TTA AGG AGA AGG GGA CGG AAA CCC CTC GAC TTC CTG ATG ATG
 Arg Trp Gly Asn Ser Ser Ser Pro Ala Phe Gly Glu Leu Lys Asp Tyr Tyr>

1230            1240            1250            1260            1270
   x       x       x       x       x       x       x       x       x       x
 CTC TTC TAC CTG AAG AGC AAG TCC CCC AAG GAG GAG CTG CTG AAG ATG TGG
 GAG AAG ATG GAC TTC TCG TTC AGG GGG TTC CTC CTC GAC GAC TTC TAC ACC
 Leu Phe Tyr Leu Lys Ser Lys Ser Pro Lys Glu Glu Leu Leu Lys Met Trp>

1280            1290            1300            1310            1320
   x       x       x       x       x       x       x       x       x       x
 GGG GAG GAG CTG ACC AGT GAA GCA AGT GTC TTT GAA GTC TTT GTT CTT TAC
 CCC CTC CTC GAC TGG TCA CTT CGT TCA CAG AAA CTT CAG AAA CAA GAA ATG
 Gly Glu Glu Leu Thr Ser Glu Ala Ser Val Phe Glu Val Phe Val Leu Tyr>

1330            1340            1350            1360            1370
   x       x       x       x       x       x       x       x       x       x
 CTC TCG GGA GAA CCA AAC CGG AAT GGT CAC AAA GTG ACT TGC CTG CCC TGG
 GAG AGC CCT CTT GGT TTG GCC TTA CCA GTG TTT CAC TGA ACG GAC GGG ACC
 Leu Ser Gly Glu Pro Asn Arg Asn Gly His Lys Val Thr Cys Leu Pro Trp>

1380            1390            1400            1410            1420
   x       x       x       x       x       x       x       x       x       x
 AAC GAT GAG CCC CTG GCG GCT GAG ACC AGC CTG CTG AAG GAG GAG CTG CTG
 TTG CTA CTC GGG GAC CGC CGA CTC TGG TCG GAC GAC TTC CTC CTC GAC GAC
 Asn Asp Glu Pro Leu Ala Ala Glu Thr Ser Leu Leu Lys Glu Glu Leu Leu>
```

FIG. 1D

```
      1430         1440         1450         1460         1470
   x      x     x      x     x      x     x      x     x      x
  CGG  GTG  AAC  CGC  CAG  GGC  ATC  CTC  ACC  ATC  AAC  TCA  CAG  CCC  AAC  ATC  AAC
  GCC  CAC  TTG  GCG  GTC  CCG  TAG  GAG  TGG  TAG  TTG  AGT  GTC  GGG  TTG  TAG  TTG
  Arg  Val  Asn  Arg  Gln  Gly  Ile  Leu  Thr  Ile  Asn  Ser  Gln  Pro  Asn  Ile  Asn>

1480         1490         1500         1510         1520         1530
   x      x     x      x     x      x     x      x     x      x     x      x
  GGG  AAG  CCG  TCC  TCC  GAC  CCC  ATC  GTG  GGC  TGG  GGC  CCC  AGC  GGG  GGC  TAT
  CCC  TTC  GGC  AGG  AGG  CTG  GGG  TAG  CAC  CCG  ACC  CCG  GGG  TCG  CCC  CCG  ATA
  Gly  Lys  Pro  Ser  Ser  Asp  Pro  Ile  Val  Gly  Trp  Gly  Pro  Ser  Gly  Gly  Tyr>

1540         1550         1560         1570         1580
         x     x      x     x      x     x      x     x      x     x
        GTC  TTC  CAG  AAG  GCC  TAC  TTA  GAG  TTT  TTC  ACT  TCC  CGC  GAG  ACA  GCG  GAA
        CAG  AAG  GTC  TTC  CGG  ATG  AAT  CTC  AAA  AAG  TGA  AGG  GCG  CTC  TGT  CGC  CTT
        Val  Phe  Gln  Lys  Ala  Tyr  Leu  Glu  Phe  Phe  Thr  Ser  Arg  Glu  Thr  Ala  Glu>

1590         1600         1610         1620         1630
     x      x     x      x     x      x     x      x     x      x
    GCA  CTT  CTG  CAA  GTG  CTG  AAG  AAG  TAC  GAG  CTC  CGG  GTT  AAT  TAC  CAC  CTT
    CGT  GAA  GAC  GTT  CAC  GAC  TTC  TTC  ATG  CTC  GAG  GCC  CAA  TTA  ATG  GTG  GAA
    Ala  Leu  Leu  Gln  Val  Leu  Lys  Lys  Tyr  Glu  Leu  Arg  Val  Asn  Tyr  His  Leu>

1640         1650         1660         1670         1680
       x      x     x      x     x      x     x      x     x      x
      GTC  AAT  GTG  AAG  GGT  GAA  AAC  ATC  ACC  AAT  GCC  CCT  GAA  CTG  CAG  CCG  AAT
      CAG  TTA  CAC  TTC  CCA  CTT  TTG  TAG  TGG  TTA  CGG  GGA  CTT  GAC  GTC  GGC  TTA
      Val  Asn  Val  Lys  Gly  Glu  Asn  Ile  Thr  Asn  Ala  Pro  Glu  Leu  Gln  Pro  Asn>

1690         1700         1710         1720         1730
       x      x     x      x     x      x     x      x     x      x
      GCT  GTC  ACT  TGG  GGC  ATC  TTC  CCT  GGG  CGA  GAG  ATC  ATC  CAG  CCC  ACC  GTA
      CGA  CAG  TGA  ACC  CCG  TAG  AAG  GGA  CCC  GCT  CTC  TAG  TAG  GTC  GGG  TGG  CAT
      Ala  Val  Thr  Trp  Gly  Ile  Phe  Pro  Gly  Arg  Glu  Ile  Ile  Gln  Pro  Thr  Val>

1740         1750         1760         1770         1780
       x      x     x      x     x      x     x      x     x      x
      GTG  GAT  CCC  GTC  AGC  TTC  ATG  TTC  TGG  AAG  GAC  GAG  GCC  TTT  GCC  CTG  TGG
      CAC  CTA  GGG  CAG  TCG  AAG  TAC  AAG  ACC  TTC  CTG  CTC  CGG  AAA  CGG  GAC  ACC
      Val  Asp  Pro  Val  Ser  Phe  Met  Phe  Trp  Lys  Asp  Glu  Ala  Phe  Ala  Leu  Trp>
```

FIG. 1E

```
     1790        1800        1810        1820        1830
  x     x     x     x     x     x     x     x     x     x
ATT GAG CGG TGG GGA AAG CTG TAT GAG GAG GAG TCC CCG TCC CGC ACC ATC
TAA CTC GCC ACC CCT TTC GAC ATA CTC CTC CTC AGG GGC AGG GCG TGG TAG
Ile Glu Arg Trp Gly Lys Leu Tyr Glu Glu Glu Ser Pro Ser Arg Thr Ile, 1840        1850        1860        1870        1880
  x     x     x     x     x     x     x     x     x     x
ATC CAG TAC ATC CAC GAC AAC TAC TTC CTG GTC AAC CTG GTG GAC AAT GAC
TAG GTC ATG TAG GTG CTG TTG ATG AAG GAC CAG TTG GAC CAC CTG TTA CTG
Ile Gln Tyr Ile His Asp Asn Tyr Phe Leu Val Asn Leu Val Asp Asn Asp, 1890        1900        1910        1920        1930
  x     x     x     x     x     x     x     x     x     x
TTC CCA CTG GAC AAC TGC CTC TGG CAG GTG GTG GAA GAC ACA TTG GAG CTT
AAG GGT GAC CTG TTG ACG GAG ACC GTC CAC CAC CTT CTG TGT AAC CTC GAA
Phe Pro Leu Asp Asn Cys Leu Trp Gln Val Val Glu Asp Thr Leu Glu Leu, 1940        1950        1960        1970        1980        1990
  x     x     x     x     x     x     x     x     x     x     x     x
CTC AAC AGG CCC ACC CAG AAT GCG AGA GAA ACG GAG GCT CCA TGACCCTGCG
GAG TTG TCC GGG TGG GTC TTA CGC TCT CTT TGC CTC CGA GGT ACTGGGACGC
Leu Asn Arg Pro Thr Gln Asn Ala Arg Glu Thr Glu Ala Pro, 2000        2010        2020        2030        2040        2050
  x     x     x     x     x     x     x     x     x     x     x     x
TCCTGACGCC CTGCGTTGGA GCCACTCCTG TCCCGCCTTC CTCCTCCACA GTGCTGCTTC
AGGACTGCGG GACGCAACCT CGGTGAGGAC AGGGCGGAAG GAGGAGGTGT CACGACGAAG 2060        2070        2080        2090        2100        2110
  x     x     x     x     x     x     x     x     x     x     x     x
TCTTGGGAAC TCCACTCTCC TTCGTGTCTC TCCCACCCCG GCCTCCACTC CCCCACCTGA
AGAACCCTTG AGGTGAGAGG AAGCACAGAG AGGGTGGGGC CGGAGGTGAG GGGGTGGACT 2120        2130        2140        2150        2160        2170
  x     x     x     x     x     x     x     x     x     x     x     x
CAATGGCAGC TAGACTGGAG TGAGGCTTCC AGGCTCTTCC TGGACCTGAG TCGGCCCCAC
GTTACCGTCG ATCTGACCTC ACTCCGAAGG TCCGAGAAGG ACCTGGACTC AGCCGGGGTG 2180        2190        2200        2210        2220
  x     x     x     x     x     x     x     x     x     x
ATGGGAACCT AGTACTCTCT GCTCTAAAAA AAAAAAAAAA AAAGGAATTC
TACCCTTGGA TCATGAGAGA CGAGATTTTT TTTTTTTTTT TTTCCTTAAG
```

Fig. 1F

```
AMVNE ARGNS SLNPC LEGSA SSGSE SSKDS SRCST PGLDP ERHER LREKM RRRLE S--GDKW FSLEF   mthfr
                                            ms ffHas qRdal nqsLa evqGqin vSfEF   ecometf
                                            ms ffHan qREal nqsLa evqGqin vSfEF   stymetf
                                                        ms iRdLy haraspf iSLEF   ysRAD1
                                    *                100·
FPPRT AEGAV NLISR FDRMA AGGPL YIDVT WHPAG DPGSD KETSS MMIAS TAVNY CGLET ILHMT    mthfr
FPPRT sEmeq tLwns iDRIs sikPk fvsVT y--ga nsGer drIhs i-Ikg ik-dr tGLEa qpHIT    ecometf
FPPRT sEmeq tLwns iDRIs sikPk fvsVT y--ga nsGer drIhs v-Ikg ik-er tGLEa qpHIT    stymetf
FPPkT elGtr NLmeR mhRMt AldPL fItVT W--ga -gGtt aEktl t-lAS lAqqt lnipv CmHlT    ysRAD1
                                *
CCRQR LEEIT GHLHK AKQLG LKNIM ALRGD -PIGDQ WEEEE GGFNY AVGLV KHIRS EFGDY FDICV   mthfr
Cidat pdEIr tiard ywnnG irhIv ALRGD lPpGsg kpE-- ---mY AsdLV tilk- EvaD- FDIsV   ecometf
Cidat rdEIr tiard ywnnG irhIv ALRGD lPpGsg kpE-- ---mY AadLV glik- EvaD- FDIsV   stymetf
Ctnte kaild daLdr CynaG irNIl ALRGn lPIGvv Wlvsq snrll nmrLf>                    ysRAD1
            200·
AGYPK GHPEA GSFEA DLKHL KEKVS AGADF IITQL FFEAD TFFRF VKACT DMGIT CPIVP GIFPI    mthfr
AqYPe vHPEA kSaqA DLInL KrKVd AGAnr aITQf FFdve sylRF rdrCv saGid veliP GIIPv    ecometf
AqYPe vHPEA kSaqA DLInL KrKVd AGAnr aITQf FFdve sylRF rdrCv saGid veliP GIIPv    stymetf
                                               300·
QGYHS LRQLV KLSKL EVPQE IKDVI EPIKD NDAAI RN-YGI ELAVS LCQEL LASGL VPGLH FYTLN   mthfr
snfkq akkfa dmtnv riPaw maqmf dgl-D dDAet RklvGa niAmd mvkiL sreG- VkdfH FYTLN   ecometf
snfkq akkfa dmtnv riPsw mslmf Egl-D nDAet RklvGa niAmd mvkiL sreG- VkdfH FYTLN   stymetf R-EMAT TEVLK RLGMW TEDPR RPLPW ALSAH PKRRE EDVRP IFWAS RPKSY IYRTD EWDEF PNGRW   mthfr
RaEMsy a-ich tLGvr pgl>                                                         ecometf
RaEMsy a-ich tLGvr pgl>                                                         stymetf
            400·
GNSSS PAFGE LKDYY LFYLK SKSPK E    mthfr
```

FIG. 2

```
AAT TCC GGA GCC ATG GTG AAC GAA GCC AGA GGA AAC AGC AGC CTC AAC CCC TGC TTG GAG   60
                Met Val Asn Glu Ala Arg Gly Asn Ser Ser Leu Asn Pro Cys Leu Glu   16

GGC AGT GCC AGC AGT GGC AGT GAG AGC TCC AAA GAT AGT TCG AGA TGT TCC ACC CCG GGC  120
Gly Ser Ala Ser Ser Gly Ser Glu Ser Ser Lys Asp Ser Ser Arg Cys Ser Thr Pro Gly   36

CTG GAC CCT GAG CGG CAT GAG AGA CTC CGG GAG AAG ATG AGG CGG CGA TTG GAA TCT GGT  180
Leu Asp Pro Glu Arg His Glu Arg Leu Arg Glu Lys Met Arg Arg Arg Leu Glu Ser Gly   56

GAC AAG TGG TTC TCC CTG GAA TTC TTC CCT CCT CGA ACT GCT GAG GGA GCT GTC AAT CTC  240
Asp Lys Trp Phe Ser Leu Glu Phe Phe Pro Pro Arg Thr Ala Glu Gly Ala Val Asn Leu   76

ATC TCA AGG TTT GAC CGG ATG GCA GCA GGT GGC CCC CTC TAC ATA GAC GTG ACC TGG CAC  300
Ile Ser Arg Phe Asp Arg Met Ala Ala Gly Gly Pro Leu Tyr Ile Asp Val Thr Trp His   96

CCA GCA GGT GAC CCT GGC TCA GAC AAG GAG ACC TCC TCC ATG ATG ATC GCC AGC ACC GCC  360
Pro Ala Gly Asp Pro Gly Ser Asp Lys Glu Thr Ser Ser Met Met Ile Ala Ser Thr Ala  116

GTG AAC TAC TGT GGC CTG GAG ACC ATC CTG CAC ATG ACC TGC TGC CGT CAG CGC CTG GAG  420
Val Asn Tyr Cys Gly Leu Glu Thr Ile Leu His Met Thr Cys Cys Arg Gln Arg Leu Glu  136

GAG ATC ACG GGC CAT CTG CAC AAA GCT AAG CAG CTG GGC CTG AAG AAC ATC ATG GCG CTG  480
Glu Ile Thr Gly His Leu His Lys Ala Lys Gln Leu Gly Leu Lys Asn Ile Met Ala Leu  156

CGG GGA GAC CCA ATA GGT GAC CAG TGG GAA GAG GAG GAG GGA GGC TTC AAC TAC GCA GTG  540
Arg Gly Asp Pro Ile Gly Asp Gln Trp Glu Glu Glu Glu Gly Gly Phe Asn Tyr Ala Val  176

GAC CTG GTG AAG CAC ATC CGA AGT GAG TTT GGT GAC TAC TTT GAC ATC TGT GTG GCA GGT  600
Asp Leu Val Lys His Ile Arg Ser Glu Phe Gly Asp Tyr Phe Asp Ile Cys Val Ala Gly  196

TAC CCC AAA GGC CAC CCC GAA GCA GGG AGC TTT GAG GCT GAC CTG AAG CAC TTG AAG GAG  660
Tyr Pro Lys Gly His Pro Glu Ala Gly Ser Phe Glu Ala Asp Leu Lys His Leu Lys Glu  216

AAG GTG TCT GCG GGA GCC GAT TTC ATC ATC ACG CAG CTT TTC TTT GAG GCT GAC ACA TTC  720
Lys Val Ser Ala Gly Ala Asp Phe Ile Ile Thr Gln Leu Phe Phe Glu Ala Asp Thr Phe  236
```

FIG. 6A

```
TTC CGC TTT GTG AAG GCA TGC ACC GAC ATG GGC ATC ACT TGC CCC ATC GTC CCC GGG ATC  780
Phe Arg Phe Val Lys Ala Cys Thr Asp Met Gly Ile Thr Cys Pro Ile Val Pro Gly Ile  256

TTT CCC ATC CAG GGC TAC CAC TCC CTT CGG CAG CTT GTG AAG CTG TCC AAG CTG GAG GTG  840
Phe Pro Ile Gln Gly Tyr His Ser Leu Arg Gln Leu Val Lys Leu Ser Lys Leu Glu Val  276

CCA CAG GAG ATC AAG GAC GTG ATT GAG CCA ATC AAA GAC AAC GAT GCT GCC ATC CGC AAC  900
Pro Gln Glu Ile Lys Asp Val Ile Glu Pro Ile Lys Asp Asn Asp Ala Ala Ile Arg Asn  296

TAT GGC ATC GAG CTG GCC GTG AGC CTG TGC CAG GAG CTT CTG GCC AGT GGC TTG GTG CCA  960
Tyr Gly Ile Glu Leu Ala Val Ser Leu Cys Gln Glu Leu Leu Ala Ser Gly Leu Val Pro  316

GGC CTC CAC TTC TAC ACC CTC AAC CGC GAG ATG GCT ACC ACA GAG GTG CTG AAG CGC CTG 1020
Gly Leu His Phe Tyr Thr Leu Asn Arg Glu Met Ala Thr Thr Glu Val Leu Lys Arg Leu  336

GGG ATG TGG ACT GAG GAC CCC AGG CGT CCC CTA CCC TGG GCT CTC AGT GCC CAC CCC AAG 1080
Gly Met Trp Thr Glu Asp Pro Arg Arg Pro Leu Pro Trp Ala Leu Ser Ala His Pro Lys  356

CGC CGA GAG GAA GAT GTA CGT CCC ATC TTC TGG GCC TCC AGA CCA AAG AGT TAC ATC TAC 1140
Arg Arg Glu Glu Asp Val Arg Pro Ile Phe Trp Ala Ser Arg Pro Lys Ser Tyr Ile Tyr  376

CGT ACC CAG GAG TGG GAC GAG TTC CCT AAC GGC CGC TGG GGC AAT TCC TCT TCC CCT GCC 1200
Arg Thr Gln Glu Trp Asp Glu Phe Pro Asn Gly Arg Trp Gly Asn Ser Ser Ser Pro Ala  396

TTT GGG GAG CTG AAG GAC TAC TAC CTC TTC TAC CTG AAG AGC AAG TCC CCC AAG GAG GAG 1260
Phe Gly Glu Leu Lys Asp Tyr Tyr Leu Phe Tyr Leu Lys Ser Lys Ser Pro Lys Glu Glu  416

CTG CTG AAG ATG TGG GGG GAG GAG CTG ACC AGT GAA GCA AGT GTC TTT GAA GTC TTT GTT 1320
Leu Leu Lys Met Trp Gly Glu Glu Leu Thr Ser Glu Ala Ser Val Phe Glu Val Phe Val  436

CTT TAC CTC TCG GGA GAA CCA AAC CGG AAT GGT CAC AAA GTG ACT TGC CTG CCC TGG AAC 1380
Leu Tyr Leu Ser Gly Glu Pro Asn Arg Asn Gly His Lys Val Thr Cys Leu Pro Trp Asn  456

GAT GAG CCC CTG GCG GCT GAG ACC AGC CTG CTG AAG GAG GAG CTG CTG CGG GTG AAC CGC 1440
Asp Glu Pro Leu Ala Ala Glu Thr Ser Leu Leu Lys Glu Glu Leu Leu Arg Val Asn Arg  476
```

FIG. 6B

```
CAG GGC ATC CTC ACC ATC AAC TCA CAG CCC AAC ATC AAC GGG AAG CCG TCC TCC GAC CCC 1500
Gln Gly Ile Leu Thr Ile Asn Ser Gln Pro Asn Ile Asn Gly Lys Pro Ser Ser Asp Pro  496

ATC GTG GGC TGG GGC CCC AGC GGG GGC TAT GTC TTC CAG AAG GCC TAC TTA GAG TTT TTC 1560
Ile Val Gly Trp Gly Pro Ser Gly Gly Tyr Val Phe Gln Lys Ala Tyr Leu Glu Phe Phe  516

ACT TCC CGC GAG ACA GCG GAA GCA CTT CTG CAA GTG CTG AAG AAG TAC GAG CTC CGG GTT 1620
Thr Ser Arg Glu Thr Ala Glu Ala Leu Leu Gln Val Leu Lys Lys Tyr Glu Leu Arg Val  536

AAT TAC CAC CTT GTC AAT GTG AAG GGT GAA AAC ATC ACC AAT GCC CCT GAA CTG CAG CCG 1680
Asn Tyr His Leu Val Asn Val Lys Gly Glu Asn Ile Thr Asn Ala Pro Glu Leu Gln Pro  556

AAT GCT GTC ACT TGG GGC ATC TTC CCT GGG CGA GAG ATC ATC CAG CCC ACC GTA GTG GAT 1740
Asn Ala Val Thr Trp Gly Ile Phe Pro Gly Arg Glu Ile Ile Gln Pro Thr Val Val Asp  576

CCC GTC AGC TTC ATG TTC TGG AAG GAC GAG GCC TTT GCC CTG TGG ATT GAG CGG TGG GGA 1800
Pro Val Ser Phe Met Phe Trp Lys Asp Glu Ala Phe Ala Leu Trp Ile Glu Arg Trp Gly  596

AAG CTG TAT GAG GAG GAG TCC CCG TCC CGC ACC ATC ATC CAG TAC ATC CAC GAC AAC TAC 1860
Lys Leu Tyr Glu Glu Glu Ser Pro Ser Arg Thr Ile Ile Gln Tyr Ile His Asp Asn Tyr  616

TTC CTG GTC AAC CTG GTG GAC AAT GAC TTC CCA CTG GAC AAC TGC CTC TGG CAG GTG GTG 1920
Phe Leu Val Asn Leu Val Asp Asn Asp Phe Pro Leu Asp Asn Cys Leu Trp Gln Val Val  636

GAA GAC ACA TTG GAG CTT CTC AAC AGG CCC ACC CAG AAT GCG AGA GAA ACG GAG GCT CCA 1980
Glu Asp Thr Leu Glu Leu Leu Asn Arg Pro Thr Gln Asn Ala Arg Glu Thr Glu Ala Pro  656

TGA CCC TGC GTC CTG ACG CCC TGC GTT GGA GCC ACT CCT GTC CCG CCT TCC TCC TCC ACA 2040
End

GTG CTG CTT CTC TTG GGA ACT CCA CTC TCC TTC GTG TCT CTC CCA CCC CGG CCT CCA CTC 2100

CCC CAC CTG ACA ATG GCA GCT AGA CTG GAG TGA GGC TTC CAG GCT CTT CCT GGA CCT GAG 2160

TCG GCC CCA CAT GGG AAC CTA GTA CTC TCT GCT CTA AAA AAA AAA AAA AAA AAG GAA TT 2220
```

FIG. 6C

```
              *
MTHFR:   KHLKEKVSAGADFIITQLFFEADTFFR
         |||  |·     || ||·||||
DHFR:    GHLKLFVT----R-IMQD-FESDTFFP
```

CDNA FOR HUMAN METHYLENETETRAHYDROFOLATE REDUCTASE

BACKGROUND OF THE INVENTION (a) Field of the Invention

The invention relates to a cDNA probe for human methylenetetrahydrofolate reductase (MTHFR), and its uses.

(b) Description of Prior Art

Folic acid derivatives are coenzymes for several critical single-carbon transfer reactions, including reactions in the biosynthesis of purines, thymidylate and methionine. Methylenetetrahydrofolate reductase (MTHFR; EC 1.5.1.20) catalyzes the NADPH-linked reduction of 5,10-methylenetetrahydrofolate to 5-methyltetrahydrofolate, a co-substrate for methylation of homocysteine to methionine. The porcine liver enzyme, a flavoprotein, has been purified to homogeneity; it is a homodimer of 77-kDa subunits. Partial proteolysis of the porcine peptide has revealed two spatially distinct domains: an N-terminal domain of 40 kDa and a C-terminal domain of 37 kDa. The latter domain contains the binding site for the allosteric regulator S-adenosylmethionine.

Hereditary deficiency of MTHFR, an autosomal recessive disorder, is the most common inborn error of folic acid metabolism. A block in the production of methyltetrahydrofolate leads to elevated homocysteine with low to normal levels of methionine. Patients with severe deficiencies of MTHFR (0–20% activity in fibroblasts) can have variable phenotypes. Developmental delay, mental retardation, motor and gait abnormalities, peripheral neuropathy, seizures and psychiatric disturbances have been reported in this group, although at least one patient with severe MTHFR deficiency was asymptomatic. Pathologic changes in the severe form include the vascular changes that have been found in other conditions with elevated homocysteine, as well as reduced neurotransmitter and methionine levels in the CNS. A milder deficiency of MTHFR (35–50% activity) has been described in patients with coronary artery disease (see below). Genetic heterogeneity is likely, considering the diverse clinical features, the variable levels of enzyme activity, and the differential heat inactivation profiles of the reductase in patients' cells.

Coronary artery disease (CAD) accounts for 25% of deaths of Canadians. Cardiovascular risk factors (male sex, family history, smoking, hypertension, dyslipoproteinemia and diabetes) account for approximately 60 to 70% of our ability to discriminate CAD patients from healthy subjects. Elevated plasma homocysteine has also been shown to be an independent risk factor for cardiovascular disease.

Homocysteine is a sulfhydryl-containing amino acid that is formed by the demethylation of methionine. It is normally metabolized to cysteine (transsulfuration) or re-methylated to methionine. Inborn errors of metabolism (as in severe MTHFR deficiency) causing extreme elevations of homocysteine in plasma, with homocystinuria, are associated with premature vascular disease and widespread arterial and venous thrombotic phenomena. Milder elevations of plasma homocysteine (as in mild MTHFR deficiency) have been associated with the development of peripheral vascular disease, cerebrovascular disease and premature CAD.

Homocysteine remethylation to methionine requires the folic acid intermediate, 5-methyltetrahydrofolate, which is produced from 5,10-methylenetetrahydrofolate folate through the action of 5,10-methylenetetrahydrofolate reductase (MTHFR). Deficiency of MTHFR results in an inability to metabolize homocysteine to methionine; elevated plasma homocysteine and decreased methionine are the metabolic consequences of the block. Severe deficiencies of MTHFR (less than 20% of activity of controls) as described above, are associated with early-onset neurologic symptoms (mental retardation, peripheral neuropathy, seizures, etc.) and with atherosclerotic changes and thromboembolism. Milder deficiencies of MTHFR (35–50% of activity of controls), with a thermolabile form of the enzyme, are seen in patients with cardiovascular disease without obvious neurologic abnormalities.

In a survey of 212 patients with proven coronary artery disease, the thermolabile form of MTHFR was found in 17% of the CAD group and 5% of controls. In a subsequent report on 339 subjects who underwent coronary angiography, a correlation was found between thermolabile MTHFR and the degree of coronary artery stenosis. Again, traditional risk factors (age, sex, smoking, hypertension, etc.) were not significantly associated with thermolabile MTHFR. All the studies on MTHFR were performed by enzymatic assays of MTHFR in lymphocytes, with measurements of activity before and after heat treatment to determine thermolability of the enzyme.

Since 5-methyltetrahydrofolate, the product of the MTHFR reaction, is the primary form of circulatory folate, a deficiency in MTHFR might lead to other types of disorders. For example, periconceptual folate administration to women reduces the occurrence and recurrence of neural tube defects in their offspring. Neural tube defects are a group of developmental malformations (meningomyelocele, anencephaly, encephalocele) that arise due to failure of closure of the neural tube. Elevated levels of plasma homocysteine have been reported in mothers of children with neural tube defects. The elevated plasma homocysteine could be due to a deficiency of MTHFR, as described above for cardiovascular disease.

Neuroblastomas are tumors derived from neural crest cells. Many of these tumors have been reported to have deletions of human chromosome region 1p36, the region of the genome to which MTHFR has been mapped. It is possible that MTHFR deletions/mutations are responsible for or contribute to the formation of this type of tumor. MTHFR abnormalities may also contribution to the formation of other types of tumors, such as colorectal tumors, since high dietary folate has been shown to be inversely associated with risk of colorectal adenomas.

MTHFR activity is required for homocysteine methylation to methionine. Methionine is necessary for the formation of S-adenosylmethionine, the primary methyl donor for methylation of DNA, proteins, lipids, neurotransmitters, etc. Abnormalities in MTHFR might lead to lower levels of methionine and S-adenosylmethionine, as well as to elevated homocysteine. Disruption of methylation processes could result in a wide variety of conditions, such as neoplasias, developmental anomalies, neurologic disorders, etc.

Although the MTHFR gene in *Escherichia coli* (metF) has been isolated and sequenced, molecular studies of the enzyme in higher organisms have been limited without the availability of a eukaryotic cDNA. In this communication, we report the isolation of a human cDNA for MTHFR, its chromosomal assignment, and the identification of mutations in MTHFR-deficient patients. This report represents the first molecular description of mutations in MTHFR deficiency.

It would be highly desirable to be provided with a cDNA probe for human methylenetetrahydrofolate reductase (MTHFR). This probe would be used for identification of sequence abnormalities in individuals with severe or mild MTHFR deficiency, including cardiovascular patients and patients with neurologic symptoms or tumors. The probe would also be used in gene therapy, isolation of the gene, and expression studies to produce the MTHFR protein. The probe would also provide the amino acid sequence of the human MTHFR protein, which would be useful for therapy of MTHFR deficiency by biochemical or pharmacological approaches.

It would be highly desirable to be provided with a molecular description of mutations in methylenetetrahydrofolate reductase deficiency.

SUMMARY OF THE INVENTION

One aim of the present invention is to provide a cDNA probe for human methylenetetrahydrofolate reductase (MTHFR).

Another aim of the present invention is to provide a molecular description of mutations in methylenetetrahydrofolate reductase deficiency.

Another aim of the present invention is to provide a nucleic acid and amino acid sequence for human methylenetetrahydrofolate reductase.

Another aim of the present invention is to provide potential therapy for individuals with methylenetetrahydrofolate reductase deficiency.

Another aim of the present invention is to provide a system for synthesis of MTHFR protein in vitro.

A further aim of the present invention is to provide for a technology/protocol for identification of sequence changes in the MTHFR gene.

BRIEF DESCRIPTION OF THE DRAWINGS

FIGS. 1A to 1F illustrate the first cDNA coding sequence (SEQ ID NO:1 and NO:2) for methylenetetrahydrofolate reductase (MTHFR);

FIG. 2 is the alignment of amino acids for human methylenetetrahydrofolate reductase (MTHFR), the metF genes from *E. Coli* (ECOMETF), and *S. Typhimurium* (STYMETF), and an unidentified open reading frame in *Saccharomyces cerevisiae* that is divergently transcribed from an excision repair gene (ysRAD1);

FIGS. 6A–6C illustrates the total available sequence (SEQ ID NO:3 and NO:4) of human MTHFR cDNA;

DETAILED DESCRIPTION OF THE INVENTION

Sequencing of Peptides from Porcine MTHFR

Figure 3A:
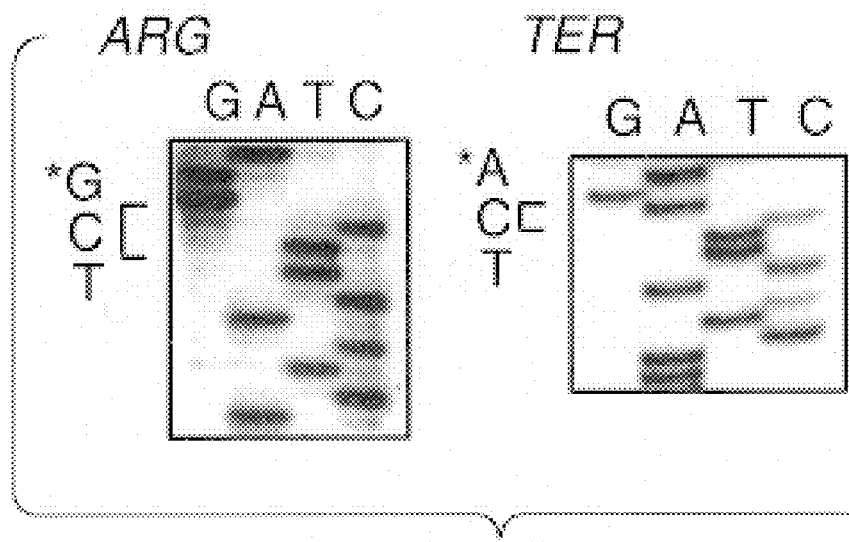
FIGS. 3A and 3B illustrate the sequencing and restriction enzyme analysis for the Arg to Ter substitution.

Homogeneous native porcine MTHFR was digested with trypsin to generate a 40 kDa N-terminal fragment and a 31 kDa C-terminal fragment; the 31 kDa fragment is a proteolytic product of the 37 kDa fragment. The fragments were separated by SDS-PAGE, electroeluted, and the denatured fragments were digested with lysyl endopeptidase (LysC). The resulting peptides were separated by reversed-phase HPLC and subjected to sequence analysis by Edman degradation (details contained in Goyette P et al., *Nature Genetics*, 1994, 7:195–200).

Isolation and Sequencing of cDNAS

Two degenerate oligonucleotides were synthesized based on the sequence of a 30 amino acid porcine MTHFR peptide (first underlined peptide in FIG. 2). These were used to generate a 90 bp PCR product, encoding the predicted peptide, from reverse transcription-PCR reactions of 500 ng pig liver polyA+RNA. A pig-specific (non-degenerate, antisense) PCR primer was then synthesized from this short cDNA sequence. Using this primer and a primer for phage arms, a human liver λgt10 cDNA library (Clontech) was screened by PCR; this technique involved the generation of phage lysate stocks (50,000 pfu) which were boiled for 5 mins and then used directly in PCR reactions with these two primers. PCR fragments were then sequenced directly (Cycle Sequencing™ kit, GIBCO), and a positive clone was identified by comparison of the deduced amino acid sequence to the sequence of the pig peptide (allowing for inter-species variations). The positive stock was then replated at lower density and screened with the radiolabelled positive PCR product by plaque hybridization until a well-isolated plaque was identified. Phage DNA was purified and the insert was then subcloned into pBS+ (Bluescript) and sequenced on both strands (Cycle Sequencing™ kit, GIBCO and Sequenase™, Pharmacia). The deduced amino acid sequence of the human cDNA was aligned to the porcine peptide sequences, the metF genes from *E.coli* (ecometf, accession number VO1502) and *S. typhimurium* (stymetf, accession number XO7689) and with a previously unidentified open reading frame in *Saccharomyces cerevisiae* that is divergently transcribed with respect to the excision repair gene, ysRAD1 (accession number KO2070). The initial alignments were performed using BestFit™ in the GCG computer package, and these alignments were adjusted manually to maximize homologies.

In summary, degenerate oligonucleotide primers were designed to amplify a sequence corresponding to a 30-amino acid segment of a porcine peptide from the N-terminal region of the enzyme (first porcine peptide in FIG. 2). A 90-bp porcine cDNA fragment was obtained from reverse transcription/PCR of pig liver RNA. Sequencing of the PCR fragment confirmed its identity by comparison of the deduced amino acid sequence to the porcine peptide sequence. A nondegenerate oligonucleotide primer, based on the internal sequence of the porcine cDNA, was used in conjunction with primers for the phage arms to screen a human liver λgt10 cDNA library by PCR. The insert of the positive clone was isolated and sequenced. The sequence consisted of 1266 bp with one continuous open reading frame.

Homology with MTHFR in Other Species

The deduced amino acid sequence of the human cDNA was aligned with the metf genes from *E.coli* and S.typhimurium, as well as with a previously unidentified ORF in Saccharomyces cerevisiae that is divergently transcribed with respect to the excision repair gene, ysRAD1 (FIG. 2). The sequences homologous to 5 porcine peptides are underlined in FIG. 2. Three segments (residues 61–94, 219–240, and 337–351) correspond to internal peptide sequence from the N-terminal 40 kDa domain of the porcine liver enzyme. Residues 374–393 correspond to the upstream portion of the LysC peptide from the C-terminal domain of the porcine liver enzyme that is labeled when the enzyme is irradiated with UV light in the presence of ($^3$H-methyl) AdoMet; as predicted from the AdoMet labeling studies, this peptide lies at one end (N-terminal) of the 37 kDa domain. A fifth region of homology (residues 359–372) was also identified, but the localization of the porcine peptide within the native protein had not been previously determined.

Methylenetetrahydrofolate reductase (MTHFR) is an enzyme involved in amino acid metabolism, that is critical for maintaining an adequate methionine pool, as well as for ensuring that the homocysteine concentration does not reach toxic levels. The high degree of sequence conservation, from E.coli to Homo sapiens, attests to the significance of MTHFR in these species. The enzyme in E. coli (encoded by the metf locus) is a 33 kDa peptide that binds reduced FAD and catalyzes the reduction of methylenetetrahydrofolate to methyltetrahydrofolate. The metf enzyme differs from the mammalian enzyme in that it cannot be reduced by NADPH or NADH, and its activity is not allosterically regulated by S-adenosylmethionine. The native porcine enzyme is susceptible to tryptic cleavage between the N-terminal 40 kDa domain and the C-terminal 37 kDa domain, and this cleavage results in the loss of allosteric regulation by adenosylmethionine, but does not result in loss of catalytic activity. Since the homology between the bacterial and mammalian enzymes is within the N-terminal domain, this region must contain the flavin binding site and residues necessary to bind the folate substrate and catalyze its reduction. The domain structure of the human enzyme has not been elucidated, although the human enzyme has been reported to have a molecular mass of 150 kDa and is likely to be a homodimer of 77 kDa.

We predict that the point of cleavage between the two domains lies between residues 351 and 374 of the human sequence, based on the localization of peptides obtained from the isolated domains of the porcine enzyme. This region, containing the highly-charged sequence KRREED, is predicted to have the highest hydrophilicity and surface probability of any region in the deduced human sequence.

The N-terminus of the porcine protein has been sequenced, and the region encoding this part of the protein is missing from the human cDNA. We estimate that this cDNA is missing only a few residues at the N-terminus, since the predicted molecular mass of the deduced sequence upstream of the putative cleavage site (KRREED) is 40 kDa, and the measured molecular mass of the porcine N-terminal domain is also 40 kDa. When the bacterial, yeast and human sequences are aligned, the deduced human sequence contains an N-terminal extension of 40 amino acids; we suspect that this extension contains determinants for NADPH binding. Many pyridine nucleotide-dependent oxidoreductases contain such determinants at the N-terminus of the protein.

The C-terminus of the human sequence contains a peptide that is labeled when the protein is irradiated with ultraviolet light in the presence of tritiated AdoMet. The cDNA sequence we report here contains only about 7 kDa of the predicted 37 kDa mass of this domain, indicating that this cDNA is truncated at the 3' terminus as well. A number of peptides from the C-terminal porcine domain have also not been detected. As might be expected, given that the prokaryotic enzymes do not appear to be allosterically regulated by AdoMet, there are no significant homologies between the C-terminal region in this cDNA and the prokaryotic metF sequences. The alignment shown in FIG. 2 shows that the homologous sequences terminate just prior to the putative cleavage site of the human enzyme.

Chromosomal Assignment

In situ hybridization to metaphase human chromosomes was used for localization of the human gene. The analysis of the distribution of 200 silver grains revealed a significant clustering of grains 40 grains, in the p36.3–36.2 region of chromosome 1 ($p<0.0001$), with the majority of grains, 25 grains, observed over 1p36.3.

The isolation of the human cDNA has allowed us to localize the gene to chromosome 1p36.3. The observation of one strong signal on that chromosome with little background is highly suggestive of a single locus with no pseudogenes. Southern blotting of human DNA revealed fragments of approximately 10 kb, predicting a gene of average size, since this cDNA encodes approximately half of the coding sequence.

Additional cDNA Sequences and Constructs for Expression Analysis

A human colon carcinoma cDNA library (gift of Dr. Nicole Beauchemin, McGill University) was screened by plaque hybridization with the original 1.3 kb cDNA to obtain additional coding sequences. A cDNA of 2.2 kb was isolated, which contained 1.3 kb of overlapping sequence to the original cDNA and 900 additional bp at the 3' end (FIG. 6). The amino acid sequence is identical to that of the original cDNA for the overlapping segment (codons 1–415) except for codon 177 (ASP) which was a GLY codon in the original cDNA. Analysis of 50 control chromosomes revealed an ASP codon at this position. The cDNA has an open reading frame of 1980 bp, 100 bp of 3' UTR and a poly A tail.

Sequencing was performed on both strands for the entire cDNA. Additional 5' sequences (800 bp) were obtained from a human kidney cDNA library (Clontech) but these sequences did not contain additional coding sequences and were therefore used for the PCR-based mutagenesis only (as described below) and not for the expression analysis. The two cDNAs (2.2 kb and 800 bp) were ligated using the EcoRI site at bp 199 and inserted into the Bluescrip™ vector (Stratagene). The 2.2 kb cDNA was subcloned into the expression. vector pTrc99A (Pharmacia) using the NcoI site at bp 11 and the XbaI site in the polylinker region of both the Bluescript™ and the pTrc99A vectors. Sequencing was performed across the cloning sites to verify the wild-type construct.

UTILITY OF INVENTION IN IDENTIFICATION OF MUTATIONS

I. Identification of First Two Mutations in Severe MTHFR Deficiency

Figure 3B:
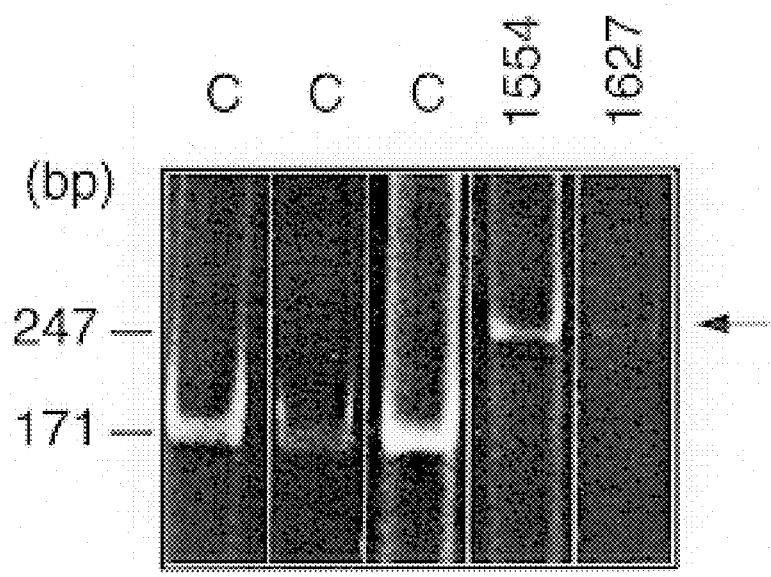

Total RNA of skin fibroblasts from MTHFR-deficient patients was reverse-transcribed and amplified by PCR for analysis by the single strand conformation polymorphism (SSCP) method (Orita, M. et al., Genomics, 1989, 5:8874–8879). Primers were designed to generate fragments of 250–300 bp and to cover the available cDNA sequences with small regions of overlap for each fragment at both ends. The first mutation identified by SSCP was a C to T substitution at bp 559 in patient 1554; this substitution converted an arginine codon to a termination codon (FIG. 3A). Since the mutation abolished a FokI site, restriction digestion was used for confirmation of the change and for screening additional patients for this mutation; a second patient (1627) was identified in this manner (FIG. 3B). The SSCP pattern for patient 1554 and the restriction digestion pattern for both patients was consistent with a homozygous mutant state or with a genetic compound consisting of the nonsense mutation with a second mutation that did not produce any detectable RNA (null allele). Studies in the parents are required for confirmation.

Figure 4A:
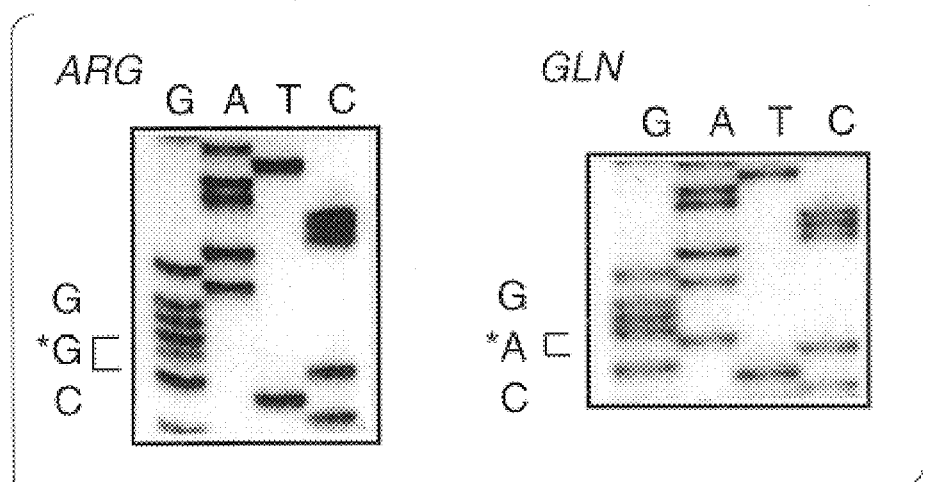
FIGS. 4A and 4B illustrate the sequencing and restriction enzyme analysis for the Arg to Gln substitution.
Figure 4B:
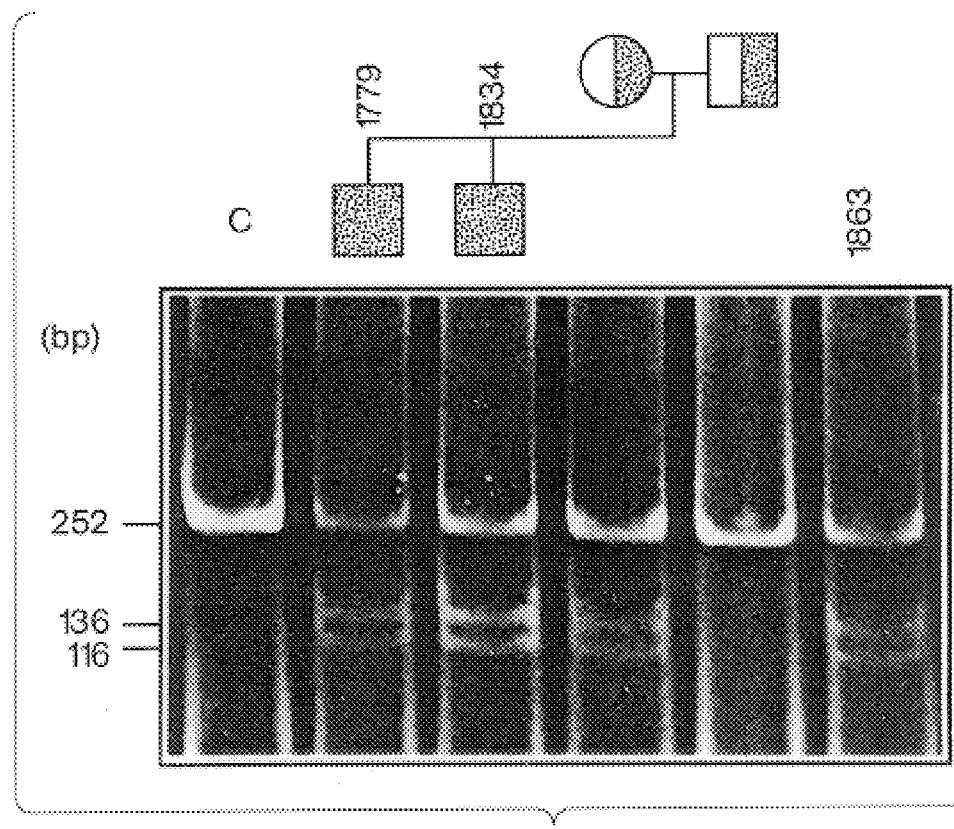

The second substitution (FIG. 4A) was a G to A transition at bp 482 in patient 1834 that converted an arginine into a glutamine residue. The substitution created a PstI site which was used to verify the substitution and to identify a second patient (1863) with this change (FIG. 4B). The SSCP analysis and the restriction digestion pattern were consistent with a heterozygous state for both patients. The arginine codon affected by this change is an evolutionarily-conserved residue, as shown in FIG. 2. This observation, in conjunction with the fact that the codon change is not conservative, makes a strong argument that the substitution is a pathologic change rather than a benign polymorphism. Furthermore, 35 controls (of similar ethnic background to that of the probands) were tested for this substitution by Southern blotting of PstI-digested DNA; all were negative.

The family of patient 1834 was studied. The symptomatic brother and the mother of the proband were all shown to carry this substitution, whereas the father was negative for the change (FIG. 4B). In the family of 1863, the mother of the proband was shown to be a carrier, while the father and an unaffected brother were negative.

Cell Lines

Cell line 1554 is from a Hopi male who was admitted at age three months with homocystinuria, seizures, dehydration, corneal clouding, hypotonia and candida sepsis. Folate distribution in cultured fibroblasts showed a *Pediococcus cerivisiae/Lactobacillus casei*(PC/LC) ratio of 0.52 (Control 0.14). There was no measurable methylenetetrahydrofolate reductase (MTHFR) activity (Control values=9.7 and 15.1 nmoles/h/mg protein; residual activity after treatment of control extracts at 55° C. for 20 min.=28% and 31%).

Cell line 1627 is from a Choctaw male who presented with poor feeding, apnea, failure to thrive, dehydration and homocystinuria at five weeks of age. He was subsequently found to have superior sagittal sinus thrombosis and hydrocephalus. The PC/LC ratio was 0.61 and the specific activity of MTHFR was 0.1 nmoles/h/mg protein. There is consanguinity in that the maternal and paternal grandmothers are thought to be "distantly related".

Cell line 1779 is from a French Canadian male with homocystinuria who first had limb weakness, incoordination, paresthesiae, and memory lapses at age 15 years, and was wheelchair-bound in his early twenties. His brother (cell line 1834) also has homocystinuria, but is 37 years old and asymptomatic. Specific activity of MTHFR was 0.7 and 0.9 nmole/h/mg protein for 1779 and 1834, respectively; the residual activity after heat treatment at 55° C. was 0.9% and 0% for 1779 and 1834, respectively.

Cell line 1863 is from a white male who was diagnosed at age 21 years because of a progressive gait disturbance, spasticity, cerebral white matter degeneration, and homocystinuria. He had a brother who died at age 21 years of neurodegenerative disease. Specific activity of MTHFR in fibroblast extracts was 1.76 nmoles/h/mg protein and the residual enzyme activity after treatment at 55° C. was 3.6%.

Mutation Analysis

Primers were designed from the cDNA sequence to generate 250–300 bp fragments which overlapped 50–75 bp at each end. The primer pairs were used in reverse transcription-PCR of 5 μg patient total fibroblast RNA. The PCR products were analyzed by a non-isotopic rapid SSCP protocol (PhastSystem™, Pharmacia), which uses direct silver staining for detection of single strands. Any PCR products from patients showing a shift on SSCP gels were purified by NuSieve (FMC Bioproducts) and sequenced directly (Cycle Sequencing™ kit, GIBCO) to identify the change. If the change affected a restriction site, then a PCR product was digested with the appropriate restriction endonuclease and analyzed on polyacrylamide gels. To screen for the Arg to Gln mutation in controls, 5 μg of PstI-digested DNA was run on 0.8% agarose gels and analyzed by Southern blotting using the radiolabelled cDNA by standard techniques.

II. Seven Additional Mutations at the Methylenetetrahydrofolate Reductase (MTHFR) Locus with Genotype: Phenotype Correlations in Severe MTHFR Deficiency It is reported hereinbelow the characterization of 7 additional mutations at this locus: 6 missense mutations and a 5' splice site defect which activates a cryptic splice site in the coding sequence. We also present a preliminary analysis of the relationship between genotype and phenotype for all 9 mutations identified thus far at this locus. A nonsense mutation and 2 missense mutations (proline to leucine and threonine to methionine) in the homozygous state are associated with extremely low activity (0–3%) and onset of symptoms within the first year. Other missense mutations (arginine to cysteine and arginine to glutamine) are associated with higher enzyme activity and later onset of symptoms.

7 additional mutations at the MTHFR locus are described and the association between genotype, enzyme activity, and clinical phenotype in severe MTHFR deficiency is examined.

Patient Description

The clinical and laboratory findings of the patients have been reported in the published literature. Residual MTHFR activity was previously measured in cultured fibroblasts at confluence.

Patient 354, an African-American girl, was diagnosed at age 13 years with mild mental retardation. Her sister, patient 355 was diagnosed at age 15 years with anorexia, tremor, hallucinations and progressive withdrawal. In patient 354, residual MTHFR activity was 19% and in her sister, 355, it was 14% of control values. The residual activity after heating had equivalent thermal stability to control enzyme.

Patient 1807, a Japanese girl whose parents are first cousins, had delayed walking and speech until age 2 years, seizures at age 6 years and a gait disturbance with peripheral neuropathy at age 16 years. Residual activity of MTHFR was 3% and the enzyme was thermolabile.

Patient 735, an African-Indian girl, was diagnosed at age 7 months with microcephaly, progressive deterioration of mental development, apnea and coma. Residual activity of MTHFR was 2% of control levels. Thermal properties were not determined.

Patient 1084, a Caucasian male, was diagnosed at age 3 months with an infantile fibrosarcoma. He was found to be hypotonic and became apneic. He died at the age of 4 months. Residual activity of MTHFR was not detectable. Thermal properties were not determined.

Patient 356, the first patient reported with MTHFR deficiency, is an Italian-American male who presented at age 16 years with muscle weakness, abnormal gait and flinging movements of the upper extremities. MTHFR residual activity was 20% of control values; activity was rapidly and exponentially inactivated at 55°.

Patient 458, a Caucasian male, was diagnosed at age 12 years with ataxia and marginal school performance. Residual MTHFR activity was approximately 10%, and the activity was thermolabile.

Patient 1396, a Caucasian female, was described as clumsy and as having a global learning disorder in childhood. At age 14 years, she developed ataxia, foot drop, and inability to walk. She developed deep vein thrombosis and bilateral pulmonary emboli. Residual activity of MTHFR was 14% and the enzyme was thermolabile.

Genomic Structure and Intronic Primers Exon nomenclature is based on available cDNA sequence in Goyette et al. (Nature Genetics, 1994, 7:195–200). Exon 1 has been arbitrarily designated as the region of cDNA from bp 1 to the first intron. Identification of introns was performed by amplification of genomic DNA using cDNA primer sequences. PCR products that were greater in size than expected cDNA sizes were sequenced directly.

Mutation Detection

Specific exons (see Table 1 for primer sequences) were amplified by PCR from genomic DNA and analyzed by the SSCP protocol. SSCP was performed with the Phastgel™ system (Pharmacia), a non-isotopic rapid SSCP protocol, as previously described (Goyette P et al., Nature Genetics, 1994, 7:195–200), or with $^{35}$S-labeled PCR products run on 6% acrylamide: 10% glycerol gels at room temperature (6 watts, over-night). In some cases, the use of restriction endonucleases, to cleave the PCR product before SSCP analysis, enhanced the detection of band shifts. PCR fragments with altered mobility were sequenced directly (GIBCO, Cycle Sequencing™ kit). If the sequence change affected a restriction endonuclease site, then the PCR product was digested with the appropriate enzyme and analyzed by PAGE. Otherwise, allele-specific oligonucleotide (ASO) hybridization was performed on a dot blot of the PCR-amplified exon.

TABLE 1

PCR Primers for DNA amplification and mutation analysis of MTHFR

| Exon | Primer Type | Primer Sequence (5'→3') | Location | Fragment Size (bp) |
|---|---|---|---|---|
| 1 | Sense | AGCCTCAACCCCTGCTTGGAGG (SEQ ID NO:5) | C | 271 |
|  | Antisense | TGACAGTTTGCTCCCCAGGCAC (SEO ID NO:6) | I |  |
| 4 | Sense | TGAAGGAGAAGGTGTCTGCGGGA (SEQ ID NO:7) | C | 198 |
|  | Antisense | AGGACGGTGCGGTGAGAGTGG (SEQ ID NO:8) | I |  |
| 5 | Sense | CACTGTGGTTGGCATGGATGATG (SEQ ID NO:9) | I | 292 |
|  | Antisense | GGCTGCTCTTGGACCCTCCTC (SEQ ID NO:10) | I |  |
| 6 | Sense | TGCTTCCGGCTCCCTCTAGCC (SEQ ID NO:11) | I | 251 |
|  | Antisense | CCTCCCGCTCCCAAGAACAAAG (SEQ ID NO:12) | I |  |

TABLE 2

Summary of genotypes, enzyme activity, age at onset, and background of patients with MTHFR deficiency

| Patient[a] | BPChanges[b] | Amino acid changes | % Activity | Age at Onset | Background |
|---|---|---|---|---|---|
| 1907 | C784T/C784T | Pro→Leu/Pro→Leu | 3 | within 1st year | Japanese |
| 735 | C9927/C692T | Thr→Met/Thr→Met | 2 | 7 months | African Indian |
| 1084 | C692T/C692T | Thr→M/Thr→Met | 0 | 3 months | Caucasian |
| 1554 | CS59T/C559T | Arg→Ter/Arg→Ter | 0 | 1 month | Native American (Hopl) |
| 1627 | C559T/C559T | Arg→Ter/Arg→Ter | 1 | 1 month | Native American (Choctaw) |
| 356 | C965T/C965T | Arg→Cys/Arg→Cys | 20 | 16 yrs | Italian American |
| 458 | C1015T/G167A | Arg→Cys/Arg→Gln | 10 | 11 yrs | Caucasian |
| 1396 | C1061T/G167A | Arg→Cys/Arg→Gln | 14 | 14 yrs | Caucasian |
| 1779[c] | G482A/7 | Arg→Gln/7 | 8 | 15 yrs | French Canadian |
| 1834[c] | G482A/7 | Arg→Gln/7 | 7 | Asymptomatic 37 yrs | French Canadian |
| 1863 | G482A/7 | Arg→Gln/7 | 14 | 21 yrs | Caucasian |
| 354[d] | 792 + 1G→A/7 | 5'splice site/7 | 19 | 13 yrs | African American |
| 355[d] | 792 + 1G→A/7 | 5'splice site/7 | 14 | 11 yrs | African American |

[a]Patients 1554 1627, 1779, 1834 and 1863 were previously reported by Goyette et al. (1994).
[b]7 = unidentified mutation.
[c]Patients 1779 and 1634 are sibs.
[d]Patients 354 and 355 are sibs.

(1) 5' Splice Site Mutation

Figure 8A:
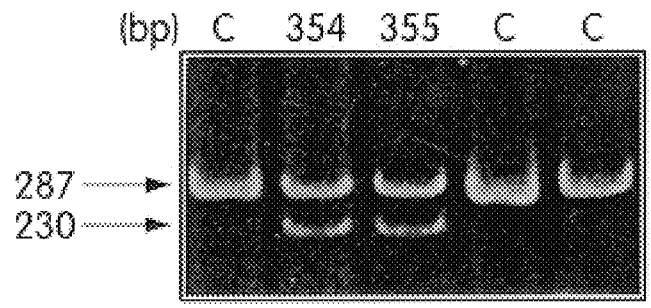
FIGS. 8A to 8D illustrate the identification of a 5' splice site mutation leading to a 57 bp in-frame deletion of the cDNA.
Figure 8B:
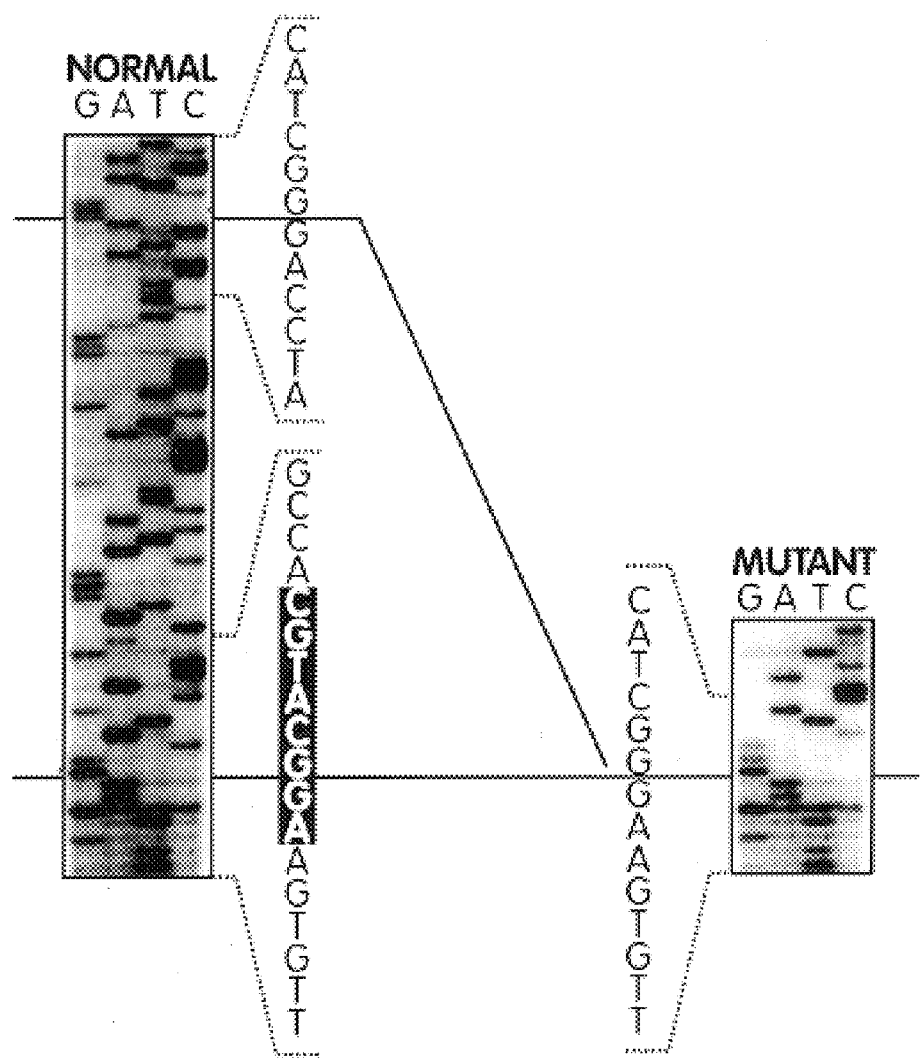
Figure 8C:
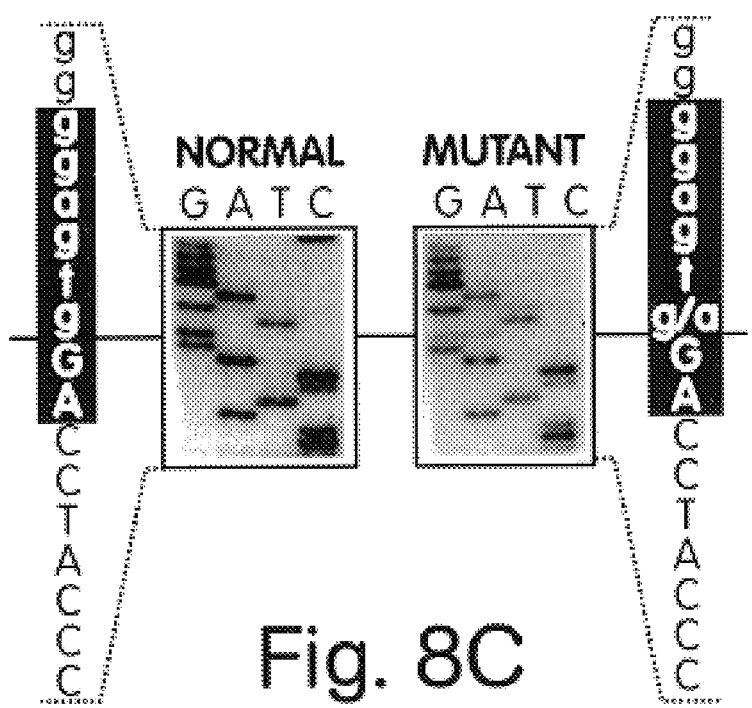
Figure 8D:
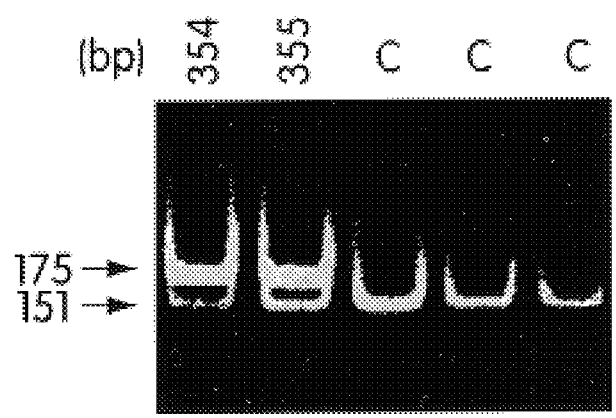

Amplification of cDNA, bp 653–939, from reverse-transcribed total fibroblast RNA revealed 2 bands in sisters 354 and 355: a smaller PCR fragment (230 bp) in addition to the normal 287 bp allele (FIG. 8A). FIG. 8A is the PAGE analysis of amplification products of cDNA bp 653–939, from reverse transcribed RNA. Controls have the expected 287 bp fragment while patients 354 and 355 have an additional 230 bp fragment. Sequencing of the smaller fragment identified a 57 bp in-frame deletion which would remove 19 amino acids (FIG. 8B). FIG. 8B is the direct sequencing of the PCR products from patient 354. The 57 bp deletion spans bp 736–792 of the cDNA. An almost perfect 5' splice site (boxed) is seen at the 5' deletion breakpoint. Analysis of the sequence at the 5' deletion breakpoint in the undeleted fragment revealed an almost perfect 5' splice site consensus sequence (AG/gcatgc). This observation suggested the presence of a splicing mutation in the natural 5' splice site that might activate this cryptic site, to generate the deleted allele. The sequence following the deletion breakpoint, in the mutant allele, corresponded exactly to the sequence of the next exon. Amplification of genomic DNA, using the same amplification primers as those used for reverse-transcribed RNA, generated a 1.2 kb PCR product indicating the presence of an intron. Direct sequencing of this PCR fragment in patient 354 identified a heterozygous G→A substitution in the conserved GT dinucleotide of the intron at the 5' splice site (FIG. 8C). FIG. 8C is the sequencing of the 5' splice site in control and patient 354. The patient carries a heterozygous G→A substitution in the 5' splice site (boxed). Intronic sequences are in lower case. This substitution abolished a HphI restriction endonuclease site which was used to confirm the mutation in the 2 sisters (FIG. 8D). FIG. 8D is the HphI restriction endonuclease analysis on PCR products of DNA for exon 4 of patients 354 and 355, and of 3 controls (C). The 198 bp PCR product has 2 HphI sites. The products of digestion for the control allele are 151, 24 and 23 bp. The products of digestion for the mutant allele are 175 and 23 bp due to the loss of a HphI site. The fragments of 24 and 23 bp have been run off the gel.

(2) Patients with Homozygous Coding Substitutions

Figure 9A:
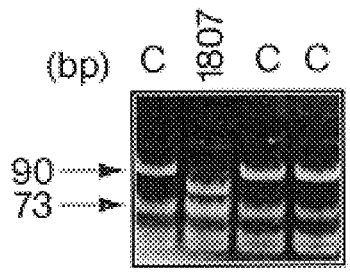
FIGS. 9A to 9D illustrate the diagnostic restriction endonuclease analysis of 4 mutations.

SSCP analysis of exon 4 for patient 1807 revealed an abnormally-migrating fragment, which was directly sequenced to reveal a homozygous C→T substitution (bp 764) converting a proline to a leucine residue. This change creates a MnlI restriction endonuclease site, which was used to confirm the homozygous state of the mutation (FIG. 9A). FIG. 9A is the MnlI restriction analysis of exon 4 PCR products for patient 1807 and 3 controls (C). Expected fragments: control allele, 90, 46, 44, 18 bp; mutant allele, 73, 46, 44, 18, 17 bp. An additional band at the bottom of the gel is the primer. Fifty independent control Caucasian chromosomes and 12 control Japanese chromosomes were tested by restriction analysis; all were negative for this mutation. Homozygosity in this patient is probably due to the consanguinity of the parents.

Figure 10A:
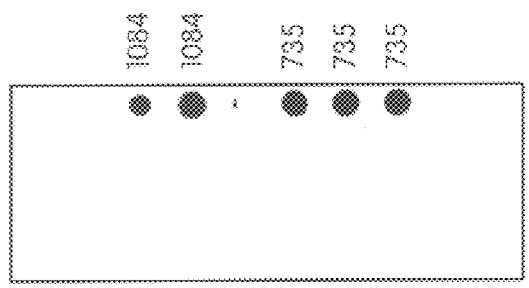
FIGS. 10A to 10D illustrate the ASO hybridization analysis of 2 mutations.
Figure 10B:
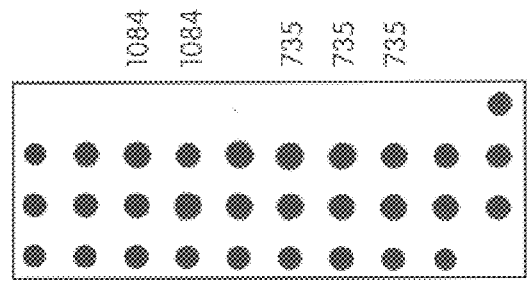

Patients 735 and 1084 had the same mutation in exon 4, in a homozygous state: a C→T substitution (bp 692) which converted an evolutionarily-conserved threonine residue to a methionine residue, and abolished a NlaIII restriction endonuclease site. Allele-specific oligonucleotide hybridization to amplified exon 4 (FIGS. 10A and 10B) was used to confirm the mutation in these 2 patients and to screen 60 independent chromosomes, all of which turned out to be negative. FIG. 10A is the hybridization of mutant oligonucleotide (692T) to exon 4 PCR products from patients 735, 1084 and 30 controls. Only DNA from patients 735 and 1084 hybridized to this probe. FIG. 10B is the hybridization of normal oligonucleotide (692C) to stripped dot blot from A. All control DNAs hybridized to this probe.

Figure 9B:
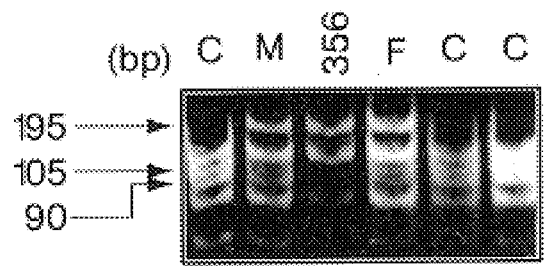

Patient 356 showed a shift on SSCP analysis of exon 5. Direct sequencing revealed a homozygous C→T substitution (bp 985) which converted an evolutionarily-conserved arginine residue to cysteine; the substitution abolished an AciI restriction endonuclease site. This was used to confirm the homozygous state of the mutation in patient 356 (FIG. 9B) and its presence in the heterozygous state in both parents. Fifty independent control chromosomes, tested in the same manner, were negative for this mutation. FIG. 9B is the AciI restriction analysis of exon 5 PCR products for patient 356, his father (F), his mother (M), and 3 controls (C). Expected fragments: control allele, 129, 105, 90, 68 bp; mutant allele, 195, 129, 68 bp.

(3) Patients Who are Genetic Compounds

Figure 10C:
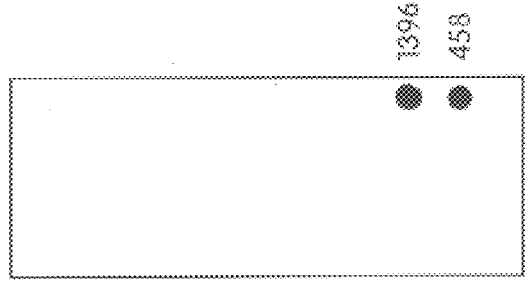
Figure 10D:
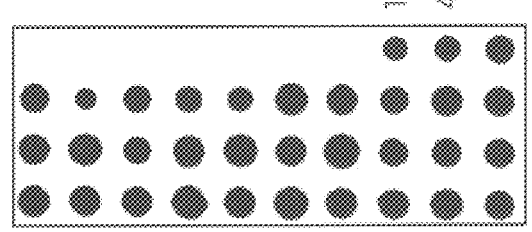
Figure 9C:
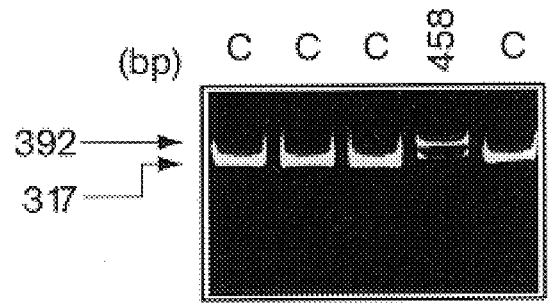

Patient 458 is a compound heterozygote of a mutation in exon 5 and a mutation in exon 1. The exon 5 substitution (C→T at bp 1015) resulted in the substitution of a cysteine residue for an arginine residue; this abolished a HhaI restriction endonuclease site, which was used to confirm the mutation in patient 458 (FIG. 9C) and to show that 50 control chromosomes were negative. FIG. 9C is the HhaI restriction analysis of exon 5 PCR products for patient 458 and 4 controls (C). Expected fragments: control allele, 317 and 75 bp; mutant allele 392 bp. The 75 bp fragment is not shown in FIG. 9C. The second mutation was a heterozygous G→A substitution (bp 167) converting an arginine to a glutamine residue. Allele-specific oligonucleotide hybridization to amplified exon 1 confirmed the heterozygous state of this mutation in patient 458 and identified a second patient (1396) carrying this mutation also in the heterozygous state (FIGS. 10C and 10D). FIG. 10C is the hybridization of mutant oligonucleotide (167A) to exon 1 PCR products from patients 458, 1396 and 31 controls. FIG. 10D is the hybridization of normal oligonucleotide (167G) to stripped dot blot from C. None of the 62 control chromosomes carried this mutation.

Figure 9D:
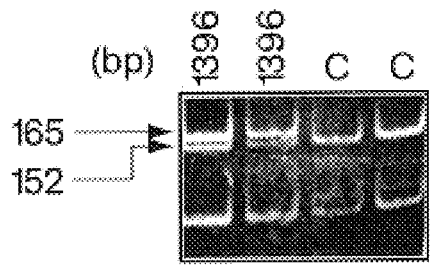

The second mutation in patient 1396 was identified in exon 6: a heterozygous C→T substitution (bp 1081) that converted an arginine residue to a cysteine residue, and abolished a HhaI restriction endonuclease site. Restriction analysis confirmed the heterozygous substitution in 1396 (FIG. 9D) and showed that 50 control chromosomes were negative. FIG. 9D is the HhaI restriction analysis of exon 6 PCR products for patient 1396 and 2 controls (C). Expected fragments: control allele, 152, 86, 13 bp; mutant allele 165, 86 bp. The 13 bp fragment has been run off the gel.

(4) Additional Sequence Changes

HhaI analysis of exon 6, mentioned above, revealed a DNA polymorphism. This change is a T→C substitution at bp 1068 which does not alter the amino acid (serine), but creates a HhaI recognition site. T at bp 1068 was found in 9% of tested chromosomes. Sequence analysis identified 2 discrepancies with the published cDNA sequence: a G→A substitution at bp 542 which converts the glycine to an aspartate codon, and a C→T change at bp 1032 which does not alter the amino acid (threonine). Since all DNAs tested (>50 chromosomes) carried the A at bp 542 and the T at bp 1032, it is likely that the sequence of the original cDNA contained some cloning artifacts.

Genotype:Phenotype Correlation

Table 2 summarizes the current status of mutations in severe MTHFR deficiency. In 8 patients, both mutations have been identified; in 5 patients (3 families), only 1 mutation has been identified. Overall the correlation between the genotype, enzyme activity, and phenotype is quite consistent. Five patients, with onset of symptoms within the first year of life, had ≦3% of control activity. Three of these patients had missense mutations in the homozygous state: two patients with the threonine to methionine substitution (C692T) and one patient with the proline to leucine substitution (C764T). The nonsense mutation (C559T) in the homozygous state in patients 1554 and 1627 (previously reported in Goyette P et al., *Nature Genetics*, 1994, 7:195–200) is also associated with a neonatal severe form, as expected.

The other patients in Table 2 had ≧6% of control activity and onset of symptoms within or after the 2nd decade of life; the only exception is patient 1834, as previously reported (Goyette P et al., Nature Genetics, 1994, 7:195–200). The three patients (356, 458 and 1396) with missense mutations (G167A, C985T, C1015T and C1081T) are similar to those previously reported (patients 1779, 1834 and 1863) who had an arginine to glutamine substitution and a second unidentified mutation (Goyette P et al., Nature Genetics, 1994, 7:195–200). The sisters with the 5' splice mutation and an unidentified second mutation also had levels of activity in the same range and onset of symptoms in the second decade, but the activity is likely due to the second unidentified allele.

Discussion

The patients come from diverse ethnic backgrounds. Although patients 1554 and 1627 are both Native Americans, the mutations occur on different haplotypes, suggesting recurrent mutation rather than identity by descent. Since the substitution occurs in a CpG dinucleotide, a "hot spot" for mutation, recurrent mutation is a reasonable hypothesis. It is difficult to assess whether some mutations are population-specific since the numbers are too small at the present time.

MTHFR deficiency is the most common inborn error of folate metabolism, and a major cause of hereditary homocysteinemia. The recent isolation of a cDNA for MTHFR has permitted mutational analysis at this locus, with the aims of defining important domains for the enzyme and of correlating genotype with phenotype in MTHFR-deficient patients.

Our definition of a disease-causing substitution, as distinct from a benign polymorphism, is based on 3 factors: (1) absence of the change in at least 50 independent control chromosomes; (2) presence of the amino acid in the bacterial enzyme, attesting to its evolutionary significance and (3) whether the change in amino acid is conservative. Although expression of the substitutions is required to formally prove that they are not benign, the criteria above allow us to postulate that the changes described in this report are likely to affect activity.

The 7 mutations described here (6 single amino acid substitutions and a 5' splice site mutation) bring the total to 9 mutations identified thus far in severe MTHFR deficiency and complete the mutation analysis for 8 patients. The identification of each mutation in only one or two families points to the striking degree of genetic heterogeneity at this locus. Seven of the 9 mutations are located in CpG dinucleotides, which are prone to mutational events.

5' Splice Site Mutation

The G→A substitution at the GT dinucleotide of the 5' splice site in patients 354 and 355 results in a 57 bp in-frame deletion of the coding sequence, which should delete 19 amino acids of the protein. This deletion occurs as a result of the activation of a cryptic 5' splice site (AG/gc) even though this cryptic site does not have a perfect 5' splice site consensus sequence (AG/gt). However, GC (instead of GT) as the first 2 nucleotides of an intron have been reported in several naturally-occurring splice sites, such as in the genes for human prothrombin and human adenine phosphoribosyltransferase and twice within the gene for the largest subunit of mouse RNA polymerase II. The remaining nucleotides of the cryptic site conform to a normal splice site consensus sequence with its expected variations ($A_{60}G_{79}/g_{100}t_{100}a_{59}a_{71}g_{82}t_{50}$). It is unlikely that the deleted enzyme resulting from this aberrantly-spliced mRNA would have any activity; 8 of the 19 deleted amino acids are conserved in the E. coli enzyme. Although the 2 patients show residual enzyme activity in the range of 20% of controls, the activity is probably due to the unidentified second allele in these patients.

6 Missense Mutations

The Arg→Cys substitution (C1081T) in patient 1396 is within a hydrophilic sequence previously postulated to be the linker region between the catalytic and regulatory domains of MTHFR (Goyette P et al., Nature Genetics, 1994, 7:195–200). These 2 domains are readily separable by mild trypsinization of the porcine enzyme. The linker domain, a highly-charged region, is likely to be located on the outside surface of the protein and therefore more accessible to proteolysis. Because the Arg→Cys substitution converts a charged hydrophilic residue to an uncharged polar residue, it cannot be considered a conservative change, and could affect the stability of the enzyme.

The 2 Arg→Cys substitutions identified in patients 356 and 458 (C985T and C1015T, respectively) may be involved in binding the FAD cofactor. Previous work in the literature showed that heating fibroblast extracts at 55°, in the absence of the FAD cofactor, inactivated MTHFR completely. The addition of FAD to the reaction mixture before heat inactivation restored some enzyme activity to control extracts and to extracts from some patients, while the extracts of patients 356 and 458 were unaffected. Based on these observations, it was suggested that these 2 patients had mutations affecting a region of the protein involved in binding FAD. The 2 mutations are found in close proximity to each other, within 11 amino acids. In patient 356, the Arg residue is evolutionarily-conserved in E. coli and is found in a stretch of 9 conserved amino acids, suggesting a critical role for this residue; the altered Arg residue in patient 458 is not evolutionarily-conserved. Crystal structure analysis of medium chain acyl-CoA dehydrogenase (MCAD), a flavoprotein, has defined critical residues involved in the binding of FAD. Two consecutive residues of the MCAD protein, Met165 and Trp166, involved in interactions with FAD, can also be identified in MTHFR, 3 and 4 amino acids downstream, respectively, from the Arg residue altered in patient 458.

Figure 7A:
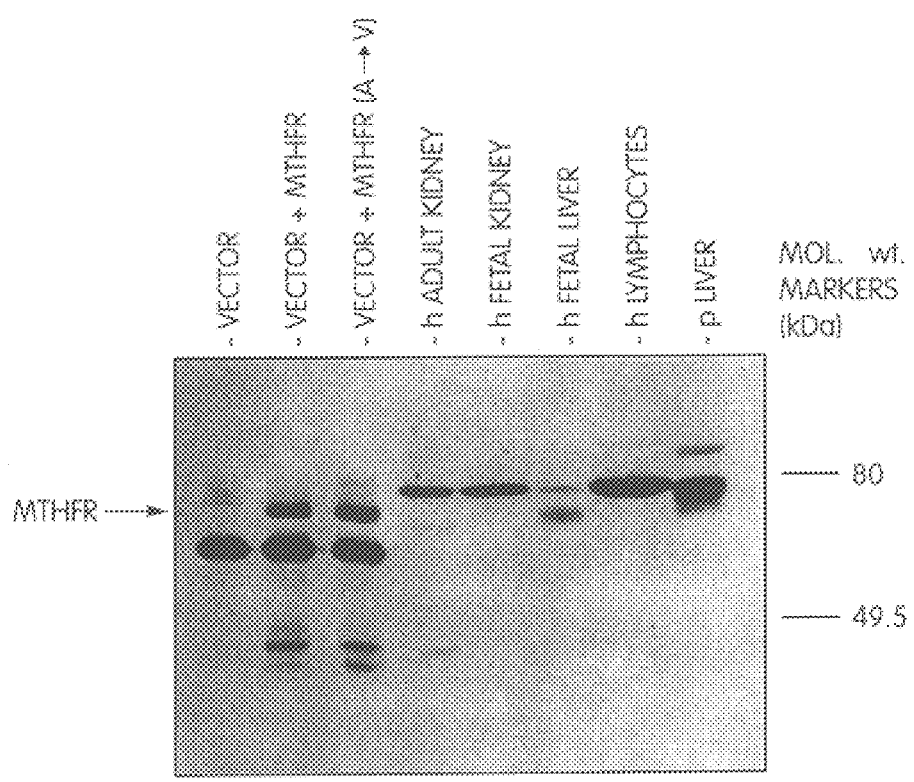
FIGS. 7A and 7B illustrate the expression analysis of MTHFR cDNA in *E. Coli*, respectively (7A) the Western blot of bacterial extracts and tissues, and (7B) the thermolability assay of bacterial extracts.
Figures 7B, 11:
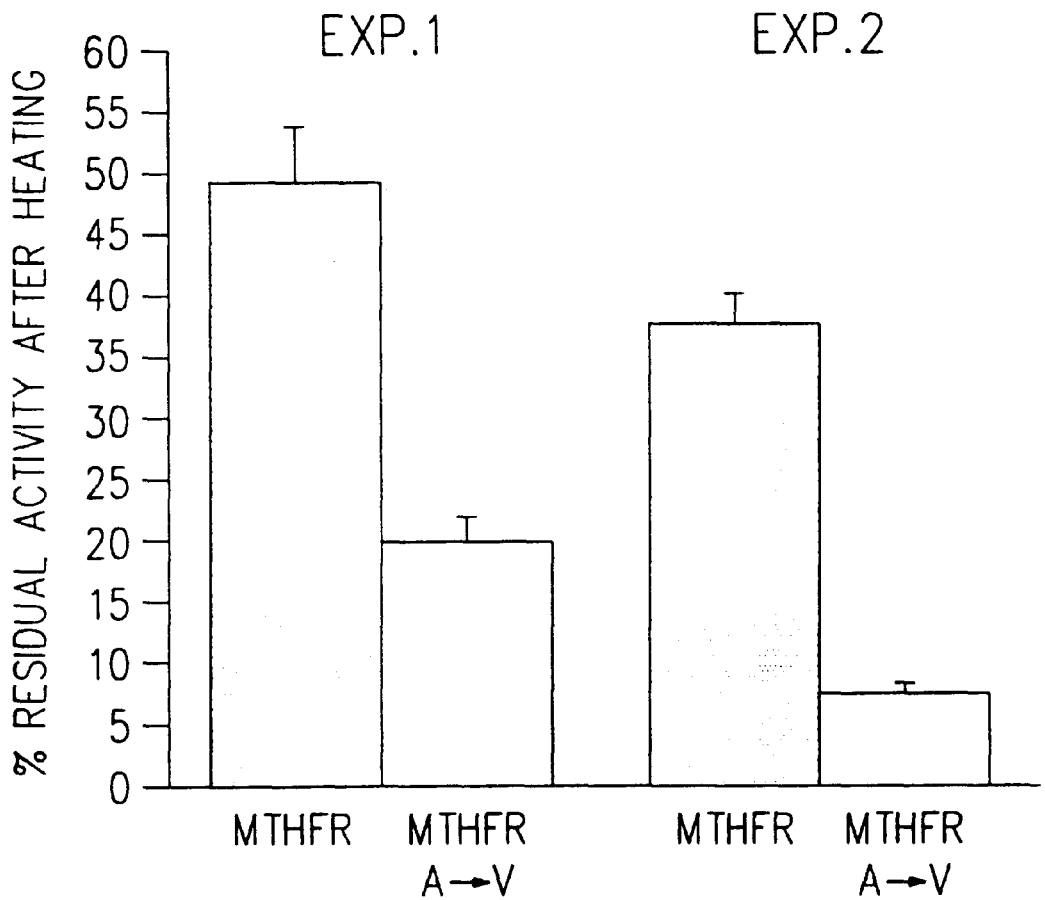
FIG. 11 illustrates the region of homology between human methylenetetrahydrofolate reductase (MTHFR) and human dihydrofolate reductase (DHFR).

The Thr→Met substitution (C692T), is found in a region of high conservation with the E. coli enzyme and in a region of good homology with human dihydrofolate reductase (DHFR) (FIG. 11). In FIG. 11,= is identity; ● is homology; and ◊ is identity to bovine DHFR enzyme. An asterisk (*) indicates location of Thr→Met substitution. Considering the early-onset phenotype of the patients, one can assume that the threonine residue is critical for activity or that it contributes to an important domain of the protein. This region of homology in DHFR contains a residue, Thr136, which has been reported to be involved in folate binding. This Thr residue in DHFR aligns with a Ser residue in MTHFR, an amino acid with similar biochemical properties. The Thr→Met substitution is located 8 amino acids downstream from this Ser codon, in the center of the region of homology between the 2 enzymes. We therefore hypothesize that the Thr→Met substitution may alter the binding of the folate substrate.

The G167A (Arg→Gln) and C764T (Pro→Leu) substitutions both affect non-conserved amino acids. Their importance in the development of MTHFR deficiency cannot be determined at the present time. All the mutations identified thus far are located in the 5' end of the coding sequence, the region thought to encode the catalytic domain of MTHFR. Mutation analysis has been useful in beginning to address the structure: function properties of the enzyme as well as to understand the diverse phenotypes in severe MTHFR deficiency.

III. Identification of A→V Mutation

Figure 5A:
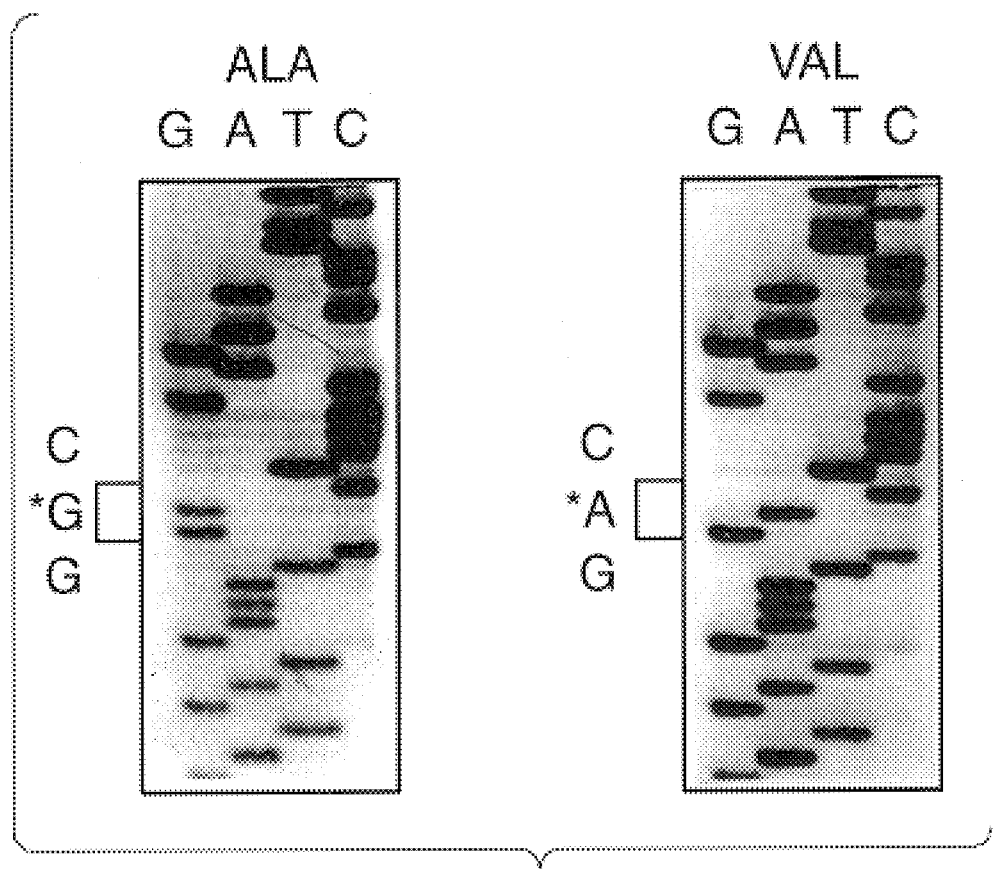
FIGS. 5A and 5B illustrates the sequence change and restriction enzyme analysis for the alanine to valine substitution.
Figure 5B:
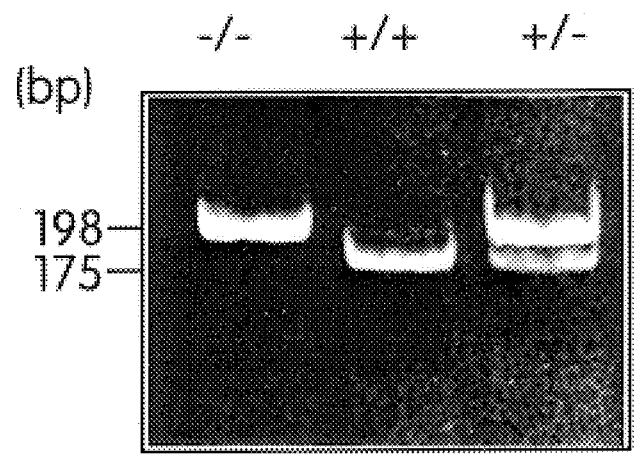

SSCP analysis and direct sequencing of PCR fragments were used to identify a C to T substitution at bp 677, which converts an alanine residue to a valine residue (FIG. 5A). The primers for analysis of the A→V change are: 5'-TGAAGGAGAA GGTGTCTGCG GGA-3' (SEQ ID NO:13) (exonic) and 5'-AGGACGGTGC GGTGAGAGTG-3' (SEQ ID NO:14) (intronic); these primers generate a fragment of 198 bp. FIG. 5A depicts the sequence of two individuals, a homozygote for the alanine residue and a homozygote for the valine residue. The antisense strands are depicted. This alteration creates a HinfI site (FIG. 5B), which was used to screen 114 unselected French Canadian chromosomes; the allele frequency of the substitution was 0.38. The substitution creates a HinfI recognition sequence which digests the 198 bp fragment into a 175 bp and a 23 bp fragment; the latter fragment has been run off the gel. FIG. 5B depicts the three possible genotypes. The frequency of the 3 genotypes were as follows: −/−, 37%; +/−, 51%; and +/+, 12% (the (+) indicates the presence of the HinfI restriction site and a valine residue).

The alanine residue is conserved in porcine MTHFR, as well as in the corresponding metF and stymetF genes of *E. Coli* and *S. Typhimurium*, respectively. The strong degree of conservation of this residue, and its location in a region of high homology with the bacterial enzymes, alluded to its importance in enzyme structure or function. Furthermore, the frequency of the (+/+) genotype was consistent with the frequency of the thermolabile MTHFR variant implicated in vascular disease.

Clinical Material

To determine the frequency of the A→V mutation, DNA from 57 individuals from Quebec was analyzed by PCR and restriction digestion. The individuals, who were all French Canadian, were not examined clinically or biochemically.

The 40 individuals analyzed in Table 3 had been previously described in Engbersen et al. (*Am. J. Hum. Genet.*, 1995, 56:142–150). Of the 13 cardiovascular patients, 8 had cerebrovascular arteriosclerosis and 5 had peripheral arteriosclerosis. Five had thermolabile MTHFR while 8 had thermostable MTHFR (greater than 33% residual activity after heating). Controls and patients were all Dutch-Caucasian, between 20–60 years of age. None of these individuals used vitamins which could alter homocysteine levels. Enzyme assays and homocysteine determinations were also reported by Engbersen et al. (*Am. J. Hum. Genet.*, 1995, 56:142–150).

TABLE 3

Correlation between MTHFR genotype and enzyme activity, thermolability and plasma homocysteine level

|  | −/− n = 19 | +/− n = 9 | +/+ n = 12 |
|---|---|---|---|
| specific activity[a,b] (nmol CH$_2$O/mg.protein/hr) | 22.9 ± 1.7 (11.8–33.8) | 15.0 ± 0.8 (10.2–18.8) | 6.9 ± 0.6 (2.6–10.2) |
| residual activity after heating[a,b] (%) | 66.8 ± 1.5 (55–76) | 56.2 ± 2.8 (41–67) | 21.8 ± 2.8 (10–35) |
| plasma homocysteine[a,c] ($\mu$M)(after fasting) | 12.6 ± 1.1 (7–21) | 13.8 ± 1.0 (9.6–20) | 22.4 ± 2.9 (9.6–42) |

TABLE 3-continued

Correlation between MTHFR genotype and enzyme activity, thermolability and plasma homocysteine level

|  | −/− n = 19 | +/− n = 9 | +/+ n = 12 |
|---|---|---|---|
| plasma homocysteine[a,c] ($\mu$M)(post-methionine load) | 41.3 ± 5.0[d] (20.9–110) | 41 ± 2.8 (29.1–54) | 72.6 ± 11.7[e] (24.4–159) |

[a] one-way anova p < .01
[b] paired t test for all combinations p < .01
[c] paired t test p < .05 for +/+ group versus +/− group or −/− group; p > .05 for +/− versus −/− group.
[d] n = 18 for this parameter
[e] n = 11 for this parameter Enzyme activity and plasma homocysteine were determined as previously reported. Each value represents mean ± standard error. The range is given in parentheses below the mean.

Correlation of A→V Mutation with Altered MTHFR Function

A genotypic analysis was performed and enzyme activity and thermolability were measured in a total of 40 lymphocyte pellets from patients with premature vascular disease and controls. 13 vascular patients were selected from a previous study (Engbersen et al., *Am. J. Hum. Genet.*, 1995, 56:142–150), among which 5 were considered to have thermolabile MTHFR. From a large reference group of 89 controls, all 7 individuals who had thermolabile MTHFR were studied, and an additional 20 controls with normal MTHFR were selected from the same reference group. Table 3 documents the relationship between genotypes and specific enzyme activity, thermolability and plasma homocysteine level. The mean MTHFR activity for individuals homozygous for the substitution (+/+) was approximately 30% of the mean activity for (−/−) individuals, homozygous for the alanine residue. Heterozygotes had a mean MTHFR activity that was 65% of the activity of (−/−) individuals; this value is intermediate between the values for (−/−) and (+/+) individuals. The ranges of activities showed some overlap for the heterozygous and (−/−) genotypes, but homozygous (+/+) individuals showed virtually no overlap with the former groups. A one-way analysis of variance yielded a p value <0.0001; a pairwise Bonferroni t test showed that all three genotypes were significantly different with p<0.01 for the three possible combinations.

The three genotypes were all significantly different (p<0.01) with respect to enzyme thermolability. The mean residual activity after heat inactivation for 5 minutes at 46° was 67%, 56% and 22% for the (−/−), (+/−) and (+/+) genotypes, respectively. While the degree of thermolability overlaps somewhat for (−/−) individuals and heterozygotes, individuals with two mutant alleles had a distinctly lower range. Every individual with the (+/+) genotype had residual activity <35% after heating, and specific activity <50% of that of the (−/−) genotype.

Total homocysteine concentrations, after fasting and 6 hours after methionine loading, were measured in plasma by high performance liquid chromatography using fluorescence detection. Fasting homocysteine levels in (+/+) individuals were almost twice the value for (+/−) and (−/−) individuals. The differences among genotypes for plasma homocysteine were maintained when homocysteine was measured following 6 hours of methionine loading. A one-way anova yielded a p<0.01 for the fasting and post-methionine homocysteine levels. A pairwise Bonferroni t test showed that only homozygous mutant individuals had significantly elevated homocysteine levels (p<0.05).

PCR-based Mutagenesis for Expression of A→V Mutation in vitro

PCR-based mutagenesis, using the cDNA-containing Bluescript™ vector as template, was used to create the A to V mutation. Vent™ polymerase (NEB) was used to reduce PCR errors. The following primers were used: primer 1, bp −200 to −178, sense; primer 2, bp 667 to 687, antisense, containing a mismatch, A, at bp 677; primer 3, 667 to 687, sense, containing a mismatch, T, at bp 677; primer 4, bp 1092 to 1114, antisense. PCR was performed using primers 1 and 2 to generate a product of 887 bp, and using primers 3 and 4 to generate a product of 447 bp. The two PCR fragments were isolated from a 1.2% agarose gel by Geneclean™ (BIO 101). A final PCR reaction, using primers 1 and 4 and the first 2 PCR fragments as template, was performed to generate a 1.3 kb band containing the mutation. The 1.3 kb fragment was digested with NcoI and MscI, and inserted into the wild-type cDNA- containing expression vector by replacing the sequences between the NcoI site at bp 11 and the MscI site at bp 943. The entire replacement fragment and the cloning sites were sequenced to verify that no additional changes were introduced by PCR.

Expression Analysis of Wild-Type and Mutagenized cDNA

Overnight cultures of JM105™ containing vector alone, vector+wild-type MTHFR cDNA, or vector+mutagenized cDNA were grown at 37° C. in 2×YT media with 0.05 mg/ml ampicillin. Fresh 10 ml. cultures of each were inoculated with approximately 50 µL of over-night cultures for a starting O.D. of 0.05, and were grown at 37° C. to an O.D. of 1 at 420 nM. Cultures were then induced for 2 hrs. with 1 mM IPTG and pelletted. The cells were resuspended in TE buffer with 2 µg/ml aprotinin and 2 µg/ml leupeptin (3.5×wet weight of cells). Cell suspensions were sonicated on ice for 3×15 sec. to break open cell membranes and then centrifuged for 30 mins. at 4° C. to pellet cell debris and unlysed cells. The supernatant was removed and assayed for protein concentration with the Bio-Rad™ protein assay. Western analysis was performed using the Amersham ECL™ kit according to the instructions of the supplier, using antiserum generated against purified porcine liver MTHFR. Enzymatic assays were performed by established procedures; thermolability was assessed by pre-treating the extracts at 46° C. for 5 mins. before determining activity. Specific activities (nmol formaldehyde/hr./mg. protein) were calculated for the 2 cDNA-containing constructs after subtraction of the values obtained with vector alone (to subtract background E. coli MTHFR activity).

The MTHFR cDNA (2.2 kb) (FIG. 6) has an open reading frame of 1980 bp, predicting a protein of 74.6 kDa. The purified porcine liver enzyme has been shown to have subunits of 77 kDa. Western analysis (FIG. 7A) of several human tissues and of porcine liver has revealed a polypeptide of 77 kDa in all the studied tissues, as well as an additional polypeptide of approximately 70 kDa in human fetal liver and in porcine liver, suggesting the presence of isozymes. Two µg of bacterial extract protein was used for lanes 1–3. The tissues (lanes 4–8) were prepared by homogenization in 0.25M sucrose with protease inhibitors (2 µg/ml each of aprotinin and leupeptin), followed by sonication (3×15 sec.) on ice. The extracts were spun for 15 min. in a microcentrifuge at 14,000 g and 100 µg of supernatant protein was used for Western analysis. h=human; p=porcine.

The wild-type cDNA and a mutagenized cDNA, containing the A→V substitution, were expressed in E. coli to yield a protein of approximately 70 kDa (FIG. 7A), which co-migrates with the smaller polypeptide mentioned above. Treatment of extracts at 46° C. for 5 minutes revealed that the enzyme containing the substitution was significantly more thermolabile than the wild-type enzyme (p<0.001; FIG. 7B). Two separate experiments (with 3–4 replicates for each construct for each experiment) were performed to measure thermostable activity of the wild-type MTHFR and mutagenized MTHFR A→V cDNAs. The values shown represent mean ±standard error for each experiment, as % of residual activity after heating. The means of the specific activities before heating (expressed as nmol formaldehyde/ hr./mg. protein) were as follows: Exp. 1, 3.8 and 5.3 for MTHFR and MTHFR A→V, respectively; Exp. 2, 6.2 and 7.5 for MTHFR and MTHFR A→V, respectively. The expression experiments were not designed to measure differences in specific activity before heating, since variation in efficiencies of expression could contribute to difficulties in interpretation. Curiously though, the specific activity for the mutant construct was higher in both experiments. It is possible that the mutant protein has increased stability in E. coli, or that inclusion bodies in our extracts contributed to differences in recovery of properly-assembled enzyme.

These studies have identified a common substitution in the MTHFR gene which results in thermolability in vitro and in vivo. The mutation, in the heterozygous or homozygous state, correlates with reduced enzyme activity and increased thermolability of MTHFR in lymphocyte extracts. A significant elevation in plasma homocysteine was observed in individuals who were homozygous for the mutation. Statistically-significant differences for homocysteine levels were not observed between heterozygotes and (−/−) individuals; this observation is not surprising, since plasma homocysteine can be influenced by several environmental factors, including intake of folate, vitamin $B_{12}$, vitamin $B_6$, and methionine, as well as by genetic variation at other loci, such as the cystathionine-β-synthase gene.

The alanine to valine substitution conserves the hydrophobicity of the residue and is associated with small changes in activity, in contrast to non-conservative changes, such as the previously-reported arginine to glutamine change in MTHFR, which is associated with a greater decrease in enzyme activity and severe hyperhomocysteinemia. The alanine residue is situated in a region of homology with the bacterial metF genes. We have also observed the same region of homology in the human dihydrofolate reductase (DHFR) gene (FIG. 11), although the alanine residue itself is not conserved; this region of amino acids 130–149 of DHFR contains T136 which has been implicated in folate binding in an analysis of the crystal structure of recombinant human DHFR. It is tempting to speculate that this region in MTHFR is also involved in folate binding and that the enzyme may be stabilized in the presence of folate. This hypothesis is compatible with the well-documented influence of folate on homocysteine levels and with the reported correction of mild hyperhomocysteinemia by folic acid in individuals with premature vascular disease, and in individuals with thermolabile MTHFR.

Although our cDNA is not long enough to encode the larger MTHFR polypeptide, it is capable of directing synthesis of the smaller isozyme. The ATG start codon for this polypeptide is within a good consensus sequence for translation initiation. Whether the isozyme is restricted to liver and what its role is in this tissue remain to be determined.

These data have identified a common genetic change in MTHFR which results in thermolability; our experiments do not directly address the relationship between this change and vascular disease. Nonetheless, this polymorphism represents a diagnostic test for evaluation of MTHFR thermolability in hyperhomocysteinemia. Large case-control studies are required to evaluate the frequency of this genetic change in various forms of occlusive arterial disease and to examine the interaction between this genetic marker and dietary factors. Well-defined populations need to be examined, since the limited data set thus far suggests that population-specific allele frequencies may exist. More importantly, however, the identification of a candidate genetic risk factor for vascular disease, which may be influenced by nutrient intake, represents a critical step in the design of appropriate therapies for the homocysteinemic form of arteriosclerosis.

cDNA FOR MTHFR AND ITS POTENTIAL UTILITY

A human cDNA for MTHFR (2.2 kb) has been isolated, as reported by us in Goyette et al. (*Nature Genetics*, 1994, 7:195–200) and Frosst et al. (*Nature Genetics*, 1995, 10:111–113). The cDNA has been expressed in vitro to yield a MTHFR protein of approximately 70 kDa (Frosst P et al., *Nature Genetics*, 1995, 10:111–113).

Using the cDNA sequence, mutations in patients with severe and mild MTHFR deficiency (Goyette P et al., *Nature Genetics*, 1994, 7:195–200; Goyette P et al., *Am. J. Hum. Genet.*, 1995, 56:1052–1059; Frosst P et al., *Nature Genetics*, 1995, 10:111–113) were identified.

The cDNA sequence is a necessary starting point for the detection of MTHFR sequence changes that would identify individuals at risk for cardiovascular and neurological diseases, as well as other disorders affected by folic acid metabolism. Diagnostic tests by DNA analysis are more efficient and accurate than testing by enzymatic/biochemical assays. Less blood is required and results are available in a shorter period of time. The tests could be performed as a routine operation in any laboratory that performs molecular genetic diagnosis, without the specialized reagents/expertise that is required for an enzymebased test.

The second major utility of the cDNA would be in the design of therapeutic protocols, for correction of MTHFR deficiency. These protocols could directly involve the gene, as in gene therapy trials or in the use of reagents that could modify gene expression. Alternatively, the therapy might require knowledge of the amino acid sequence (derived from the cDNA sequence), as in the use of reagents that would modify enzyme activity. The identification of sequences and/or sequence changes in specific regions of the cDNA or protein, such as FAD binding sites or folate-binding sites, are useful in designing therapeutic protocols involving the above nutrients.

UTILITY OF INVENTION IN CLINICAL AND DIAGNOSTIC STUDIES

Coronary artery disease patients in Montreal (n=153) were studied to examine the frequency of the alanine to valine substitution. Fourteen percent of the patients were homozygous for this mutation. An analysis of 70 control individuals (free of cardiovascular disease) demonstrated that only seven % of these individuals were homozygous for the alanine to valine mutation.

Analysis of homocysteine levels in 123 men of the above patient group indicated that the mutant allele significantly raised homocysteine levels from 10.2 micromoles/L in homozygous normal men to 11.5 and 12.7 in heterozygotes and homozygous mutants, respectively.

Families with a child with spina bifida, a neural tube defect, have been examined for the presence of the alanine to valine mutation. Approximately 16% of mothers who had a child with spina bifida were homozygous for this mutation, while only 5% of control individuals were homozygous. Fathers of children with spina bifida also had an increased prevalence of the homozygous mutant genotype (10%) as did the affected children themselves (13%).

Table 4 indicates the interactive effect of folic acid with the homozygous mutant alanine to valine change. In a study of families from Framingham, Mass. and Utah, individuals who were homozygous mutant but had folate levels above 5 ng/ml did not have increased homocysteine levels compared to individuals with the normal or heterozygous genotype. However, individuals who were homozygous mutant but had folate levels below 5 ng/ml had homocysteine levels that were significantly higher than the other genotypes.

TABLE 4

Mean fasting and PML homocysteine levels for different MTHFR genotypes

| Plasma Homocysteine | MTHFR genotype | | | |
|---|---|---|---|---|
| | Normals (−/−) | Heterozygotes (+/−) | Homozygotes (+/+) | $P_{trend}$ |
| N | 58 | 61 | 30 | |
| Fasting* | 9.4 | 9.2 | 12.1 | 0.02 |
| Folate < 5 ng/mL | 10.2 | 10.4 | 15.2 | 0.002 |
| Folate ≥ 5 ng/mL | 8.2 | 7.5 | 7.5 | 0.52 |
| Post-Methionine load | 30.0 | 30.9 | 31.3 | 0.62 |

*Significant interaction between folate levels and genotype (p = 0.03)

Example III provides preliminary data for therapeutic intervention by folic acid supplementation to individuals who are homozygous for the alanine to valine change. The data suggest that higher levels of plasma folate would lead to normalization of homocysteine levels in mutant individuals and might prevent the occurrence of disorders associated with high homocysteine levels, such as cardiovascular disease, neural tube defects, and possibly other disorders. Folic acid supplementation for mutant individuals might also restore methionine and S-adenosylmethionine levels to normal. This would be relevant for disorders that are influenced by methylation, such as neoplasias, developmental anomalies, neurologic disease, etc.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A cDNA probe for a human methylenetetrahydrofolate reductase (MTHFR) gene, said probe comprising a nucleotide sequence as set forth in SEQ ID NO:1 or a nucleoude sequence which encodes an amino acid sequence as set forth in SEQ ID NO: 2.

2. A method of diagnosis of methylenetetrahydrofolate reductase (MTHFR) deficiency in a patient which comprises the steps of:

a) amplifying a DNA sample from said patient or reverse-transcribing an RNA sample from said patient into DNA and amplifying said DNA; and b) analyzing the amplified DNA of step a) to determine whether said sample comprises at least one disease-causing sequence abnormality with respect to the human MTHFR nucleotide sequence as set forth in SEQ ID NO: 1 or a sequence encoding the human MTHFR amino acid sequence as set forth in SEQ ID NO: 2, said abnormality leading to a decrease in MTHFR activity and being indicative of MTHFR deficiency.

3. The method of claim 2, wherein said MTHFR deficiency is associated with a disorder selected from the group consisting of cardiovascular disorders, cancer, neurological disorders, and disorders influenced by folic acid metabolism.

4. The method of claim 2, wherein said sequence abnormality comprises a mutation selected from the group consisting of 167G→A, 482G→A, 559C→T, 677C→T, 692C→T, 764C→T, 792+1A→T, 985C→T, 1015C→T, and 1081C→T.

5. The diagnosis method of claim 2, wherein said MTHFR deficiency is associated with an increased risk of occurrence of a neural tube defect in an offspring of said patient.

6. The method of claim 3, wherein said cancer is selected from the group consisting of neuroblastomas and colorectal carcinomas.

7. The method of diagnosis of claim 4, wherein said sequence abnormality consists of the 677C→T sequence abnormality.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 2220 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION:1..1980

(xi) SEQUENCE DESCRIPTION: SEQ ID NO: 1:

```
AAT TCC GGA GCC ATG GTG AAC GAA GCC AGA GGA AAC AGC AGC CTC AAC        48
Asn Ser Gly Ala Met Val Asn Glu Ala Arg Gly Asn Ser Ser Leu Asn
 1               5                  10                  15

CCC TGC TTG GAG GGC AGT GCC AGC AGT GGC AGT GAG AGC TCC AAA GAT        96
Pro Cys Leu Glu Gly Ser Ala Ser Ser Gly Ser Glu Ser Ser Lys Asp
                20                  25                  30

AGT TCG AGA TGT TCC ACC CCG GGC CTG GAC CCT GAG CGG CAT GAG AGA       144
Ser Ser Arg Cys Ser Thr Pro Gly Leu Asp Pro Glu Arg His Glu Arg
            35                  40                  45

CTC CGG GAG AAG ATG AGG CGG CGA TTG GAA TCT GGT GAC AAG TGG TTC       192
Leu Arg Glu Lys Met Arg Arg Arg Leu Glu Ser Gly Asp Lys Trp Phe
        50                  55                  60

TCC CTG GAA TTC TTC CCT CCT CGA ACT GCT GAG GGA GCT GTC AAT CTC       240
Ser Leu Glu Phe Phe Pro Pro Arg Thr Ala Glu Gly Ala Val Asn Leu
 65                  70                  75                  80

ATC TCA AGG TTT GAC CGG ATG GCA GCA GGT GGC CCC CTC TAC ATA GAC       288
Ile Ser Arg Phe Asp Arg Met Ala Ala Gly Gly Pro Leu Tyr Ile Asp
                85                  90                  95

GTG ACC TGG CAC CCA GCA GGT GAC CCT GGC TCA GAC AAG GAG ACC TCC       336
Val Thr Trp His Pro Ala Gly Asp Pro Gly Ser Asp Lys Glu Thr Ser
                100                 105                 110

TCC ATG ATG ATC GCC AGC ACC GCC GTG AAC TAC TGT GGC CTG GAG ACC       384
Ser Met Met Ile Ala Ser Thr Ala Val Asn Tyr Cys Gly Leu Glu Thr
            115                 120                 125

ATC CTG CAC ATG ACC TGC TGC CGT CAG CGC CTG GAG GAG ATC ACG GGC       432
Ile Leu His Met Thr Cys Cys Arg Gln Arg Leu Glu Glu Ile Thr Gly
        130                 135                 140

CAT CTG CAC AAA GCT AAG CAG CTG GGC CTG AAG AAC ATC ATG GCG CTG       480
His Leu His Lys Ala Lys Gln Leu Gly Leu Lys Asn Ile Met Ala Leu
145                 150                 155                 160

CGG GGA GAC CCA ATA GGT GAC CAG TGG GAA GAG GAG GAG GGA GGC TTC       528
Arg Gly Asp Pro Ile Gly Asp Gln Trp Glu Glu Glu Glu Gly Gly Phe
                165                 170                 175

AAC TAC GCA GTG GAC CTG GTG AAG CAC ATC CGA AGT GAG TTT GGT GAC       576
Asn Tyr Ala Val Asp Leu Val Lys His Ile Arg Ser Glu Phe Gly Asp
                180                 185                 190

TAC TTT GAC ATC TGT GTG GCA GGT TAC CCC AAA GGC CAC CCC GAA GCA       624
Tyr Phe Asp Ile Cys Val Ala Gly Tyr Pro Lys Gly His Pro Glu Ala
            195                 200                 205
```

```
GGG AGC TTT GAG GCT GAC CTG AAG CAC TTG AAG GAG AAG GTG TCT GCG      672
Gly Ser Phe Glu Ala Asp Leu Lys His Leu Lys Glu Lys Val Ser Ala
    210                 215                 220

GGA GCC GAT TTC ATC ATC ACG CAG CTT TTC TTT GAG GCT GAC ACA TTC      720
Gly Ala Asp Phe Ile Ile Thr Gln Leu Phe Phe Glu Ala Asp Thr Phe
225                 230                 235                 240

TTC CGC TTT GTG AAG GCA TGC ACC GAC ATG GGC ATC ACT TGC CCC ATC      768
Phe Arg Phe Val Lys Ala Cys Thr Asp Met Gly Ile Thr Cys Pro Ile
                245                 250                 255

GTC CCC GGG ATC TTT CCC ATC CAG GGC TAC CAC TCC CTT CGG CAG CTT      816
Val Pro Gly Ile Phe Pro Ile Gln Gly Tyr His Ser Leu Arg Gln Leu
            260                 265                 270

GTG AAG CTG TCC AAG CTG GAG GTG CCA CAG GAG ATC AAG GAC GTG ATT      864
Val Lys Leu Ser Lys Leu Glu Val Pro Gln Glu Ile Lys Asp Val Ile
        275                 280                 285

GAG CCA ATC AAA GAC AAC GAT GCT GCC ATC CGC AAC TAT GGC ATC GAG      912
Glu Pro Ile Lys Asp Asn Asp Ala Ala Ile Arg Asn Tyr Gly Ile Glu
    290                 295                 300

CTG GCC GTG AGC CTG TGC CAG GAG CTT CTG GCC AGT GGC TTG GTG CCA      960
Leu Ala Val Ser Leu Cys Gln Glu Leu Leu Ala Ser Gly Leu Val Pro
305                 310                 315                 320

GGC CTC CAC TTC TAC ACC CTC AAC CGC GAG ATG GCT ACC ACA GAG GTG     1008
Gly Leu His Phe Tyr Thr Leu Asn Arg Glu Met Ala Thr Thr Glu Val
                325                 330                 335

CTG AAG CGC CTG GGG ATG TGG ACT GAG GAC CCC AGG CGT CCC CTA CCC     1056
Leu Lys Arg Leu Gly Met Trp Thr Glu Asp Pro Arg Arg Pro Leu Pro
            340                 345                 350

TGG GCT CTC AGT GCC CAC CCC AAG CGC CGA GAG GAA GAT GTA CGT CCC     1104
Trp Ala Leu Ser Ala His Pro Lys Arg Arg Glu Glu Asp Val Arg Pro
        355                 360                 365

ATC TTC TGG GCC TCC AGA CCA AAG AGT TAC ATC TAC CGT ACC CAG GAG     1152
Ile Phe Trp Ala Ser Arg Pro Lys Ser Tyr Ile Tyr Arg Thr Gln Glu
    370                 375                 380

TGG GAC GAG TTC CCT AAC GGC CGC TGG GGC AAT TCC TCT TCC CCT GCC     1200
Trp Asp Glu Phe Pro Asn Gly Arg Trp Gly Asn Ser Ser Ser Pro Ala
385                 390                 395                 400

TTT GGG GAG CTG AAG GAC TAC TAC CTC TTC TAC CTG AAG AGC AAG TCC     1248
Phe Gly Glu Leu Lys Asp Tyr Tyr Leu Phe Tyr Leu Lys Ser Lys Ser
                405                 410                 415

CCC AAG GAG GAG CTG CTG AAG ATG TGG GGG GAG GAG CTG ACC AGT GAA     1296
Pro Lys Glu Glu Leu Leu Lys Met Trp Gly Glu Glu Leu Thr Ser Glu
            420                 425                 430

GCA AGT GTC TTT GAA GTC TTT GTT CTT TAC CTC TCG GGA GAA CCA AAC     1344
Ala Ser Val Phe Glu Val Phe Val Leu Tyr Leu Ser Gly Glu Pro Asn
        435                 440                 445

CGG AAT GGT CAC AAA GTG ACT TGC CTG CCC TGG AAC GAT GAG CCC CTG     1392
Arg Asn Gly His Lys Val Thr Cys Leu Pro Trp Asn Asp Glu Pro Leu
    450                 455                 460

GCG GCT GAG ACC AGC CTG CTG AAG GAG GAG CTG CTG CGG GTG AAC CGC     1440
Ala Ala Glu Thr Ser Leu Leu Lys Glu Glu Leu Leu Arg Val Asn Arg
465                 470                 475                 480

CAG GGC ATC CTC ACC ATC AAC TCA CAG CCC AAC ATC AAC GGG AAG CCG     1488
Gln Gly Ile Leu Thr Ile Asn Ser Gln Pro Asn Ile Asn Gly Lys Pro
                485                 490                 495

TCC TCC GAC CCC ATC GTG GGC TGG GGC CCC AGC GGG GGC TAT GTC TTC     1536
Ser Ser Asp Pro Ile Val Gly Trp Gly Pro Ser Gly Gly Tyr Val Phe
            500                 505                 510

CAG AAG GCC TAC TTA GAG TTT TTC ACT TCC CGC GAG ACA GCG GAA GCA     1584
Gln Lys Ala Tyr Leu Glu Phe Phe Thr Ser Arg Glu Thr Ala Glu Ala
```

-continued

```
            515                 520                 525
CTT CTG CAA GTG CTG AAG AAG TAC GAG CTC CGG GTT AAT TAC CAC CTT    1632
Leu Leu Gln Val Leu Lys Lys Tyr Glu Leu Arg Val Asn Tyr His Leu
        530                 535                 540

GTC AAT GTG AAG GGT GAA AAC ATC ACC AAT GCC CCT GAA CTG CAG CCG    1680
Val Asn Val Lys Gly Glu Asn Ile Thr Asn Ala Pro Glu Leu Gln Pro
545                 550                 555                 560

AAT GCT GTC ACT TGG GGC ATC TTC CCT GGG CGA GAG ATC ATC CAG CCC    1728
Asn Ala Val Thr Trp Gly Ile Phe Pro Gly Arg Glu Ile Ile Gln Pro
                565                 570                 575

ACC GTA GTG GAT CCC GTC AGC TTC ATG TTC TGG AAG GAC GAG GCC TTT    1776
Thr Val Val Asp Pro Val Ser Phe Met Phe Trp Lys Asp Glu Ala Phe
            580                 585                 590

GCC CTG TGG ATT GAG CGG TGG GGA AAG CTG TAT GAG GAG GAG TCC CCG    1824
Ala Leu Trp Ile Glu Arg Trp Gly Lys Leu Tyr Glu Glu Glu Ser Pro
        595                 600                 605

TCC CGC ACC ATC ATC CAG TAC ATC CAC GAC AAC TAC TTC CTG GTC AAC    1872
Ser Arg Thr Ile Ile Gln Tyr Ile His Asp Asn Tyr Phe Leu Val Asn
    610                 615                 620

CTG GTG GAC AAT GAC TTC CCA CTG GAC AAC TGC CTC TGG CAG GTG GTG    1920
Leu Val Asp Asn Asp Phe Pro Leu Asp Asn Cys Leu Trp Gln Val Val
625                 630                 635                 640

GAA GAC ACA TTG GAG CTT CTC AAC AGG CCC ACC CAG AAT GCG AGA GAA    1968
Glu Asp Thr Leu Glu Leu Leu Asn Arg Pro Thr Gln Asn Ala Arg Glu
                645                 650                 655

ACG GAG GCT CCA TGACCCTGCG TCCTGACGCC CTGCGTTGGA GCCACTCCTG        2020
Thr Glu Ala Pro
            660

TCCCGCCTTC CTCCTCCACA GTGCTGCTTC TCTTGGGAAC TCCACTCTCC TTCGTGTCTC  2080

TCCCACCCCG GCCTCCACTC CCCCACCTGA CAATGGCAGC TAGACTGGAG TGAGGCTTCC  2140

AGGCTCTTCC TGGACCTGAG TCGGCCCCAC ATGGGAACCT AGTACTCTCT GCTCTAAAAA  2200

AAAAAAAAAA AAAGGAATTC                                             2220
```

(2) INFORMATION FOR SEQ ID NO: 2:

(i) SEQUENCE CHARACTERISTICS:
        (A) LENGTH: 660 amino acids
        (B) TYPE: amino acid
        (D) TOPOLOGY: linear (ii) MOLECULE TYPE: protein (xi) SEQUENCE DESCRIPTION: SEQ ID NO: 2:

```
Asn Ser Gly Ala Met Val Asn Glu Ala Arg Gly Asn Ser Ser Leu Asn
1               5                   10                  15

Pro Cys Leu Glu Gly Ser Ala Ser Ser Gly Ser Glu Ser Ser Lys Asp
            20                  25                  30

Ser Ser Arg Cys Ser Thr Pro Gly Leu Asp Pro Glu His Glu Arg
        35                  40                  45

Leu Arg Glu Lys Met Arg Arg Leu Glu Ser Gly Asp Lys Trp Phe
    50                  55                  60

Ser Leu Glu Phe Phe Pro Pro Arg Thr Ala Glu Gly Ala Val Asn Leu
65                  70                  75                  80

Ile Ser Arg Phe Asp Arg Met Ala Ala Gly Gly Pro Leu Tyr Ile Asp
                85                  90                  95

Val Thr Trp His Pro Ala Gly Asp Pro Gly Ser Asp Lys Glu Thr Ser
            100                 105                 110
```

```
Ser Met Met Ile Ala Ser Thr Ala Val Asn Tyr Cys Gly Leu Glu Thr
        115                 120                 125

Ile Leu His Met Thr Cys Cys Arg Gln Arg Leu Glu Glu Ile Thr Gly
130                 135                 140

His Leu His Lys Ala Lys Gln Leu Gly Leu Lys Asn Ile Met Ala Leu
145                 150                 155                 160

Arg Gly Asp Pro Ile Gly Asp Gln Trp Glu Glu Glu Gly Gly Phe
                165                 170                 175

Asn Tyr Ala Val Asp Leu Val Lys His Ile Arg Ser Glu Phe Gly Asp
            180                 185                 190

Tyr Phe Asp Ile Cys Val Ala Gly Tyr Pro Lys Gly His Pro Glu Ala
        195                 200                 205

Gly Ser Phe Glu Ala Asp Leu Lys His Leu Lys Glu Lys Val Ser Ala
    210                 215                 220

Gly Ala Asp Phe Ile Ile Thr Gln Leu Phe Phe Glu Ala Asp Thr Phe
225                 230                 235                 240

Phe Arg Phe Val Lys Ala Cys Thr Asp Met Gly Ile Thr Cys Pro Ile
                245                 250                 255

Val Pro Gly Ile Phe Pro Ile Gln Gly Tyr His Ser Leu Arg Gln Leu
                260                 265                 270

Val Lys Leu Ser Lys Leu Glu Val Pro Gln Glu Ile Lys Asp Val Ile
            275                 280                 285

Glu Pro Ile Lys Asp Asn Asp Ala Ala Ile Arg Asn Tyr Gly Ile Glu
            290                 295                 300

Leu Ala Val Ser Leu Cys Gln Glu Leu Leu Ala Ser Gly Leu Val Pro
305                 310                 315                 320

Gly Leu His Phe Tyr Thr Leu Asn Arg Glu Met Ala Thr Thr Glu Val
                325                 330                 335

Leu Lys Arg Leu Gly Met Trp Thr Glu Asp Pro Arg Arg Pro Leu Pro
                340                 345                 350

Trp Ala Leu Ser Ala His Pro Lys Arg Arg Glu Glu Asp Val Arg Pro
            355                 360                 365

Ile Phe Trp Ala Ser Arg Pro Lys Ser Tyr Ile Tyr Arg Thr Gln Glu
            370                 375                 380

Trp Asp Glu Phe Pro Asn Gly Arg Trp Gly Asn Ser Ser Pro Ala
385                 390                 395                 400

Phe Gly Glu Leu Lys Asp Tyr Tyr Leu Phe Tyr Leu Lys Ser Lys Ser
                405                 410                 415

Pro Lys Glu Glu Leu Leu Lys Met Trp Gly Glu Glu Leu Thr Ser Glu
                420                 425                 430

Ala Ser Val Phe Glu Val Phe Val Leu Tyr Leu Ser Gly Glu Pro Asn
            435                 440                 445

Arg Asn Gly His Lys Val Thr Cys Leu Pro Trp Asn Asp Glu Pro Leu
    450                 455                 460

Ala Ala Glu Thr Ser Leu Leu Lys Glu Glu Leu Leu Arg Val Asn Arg
465                 470                 475                 480

Gln Gly Ile Leu Thr Ile Asn Ser Gln Pro Asn Ile Asn Gly Lys Pro
                485                 490                 495

Ser Ser Asp Pro Ile Val Gly Trp Gly Pro Ser Gly Tyr Val Phe
                500                 505                 510

Gln Lys Ala Tyr Leu Glu Phe Phe Thr Ser Arg Glu Thr Ala Glu Ala
            515                 520                 525

Leu Leu Gln Val Leu Lys Lys Tyr Glu Leu Arg Val Asn Tyr His Leu
```

```
                  530                 535                 540
Val Asn Val Lys Gly Glu Asn Ile Thr Asn Ala Pro Glu Leu Gln Pro
545                 550                 555                 560

Asn Ala Val Thr Trp Gly Ile Phe Pro Gly Arg Glu Ile Ile Gln Pro
                    565                 570                 575

Thr Val Val Asp Pro Val Ser Phe Met Phe Trp Lys Asp Glu Ala Phe
                580                 585                 590

Ala Leu Trp Ile Glu Arg Trp Gly Lys Leu Tyr Glu Glu Ser Pro
                595                 600                 605

Ser Arg Thr Ile Ile Gln Tyr Ile His Asp Asn Tyr Phe Leu Val Asn
            610                 615                 620

Leu Val Asp Asn Asp Phe Pro Leu Asp Asn Cys Leu Trp Gln Val Val
625                 630                 635                 640

Glu Asp Thr Leu Glu Leu Leu Asn Arg Pro Thr Gln Asn Ala Arg Glu
                645                 650                 655

Thr Glu Ala Pro
            660
```

(2) INFORMATION FOR SEQ ID NO: 3:

(i) SEQUENCE CHARACTERISTICS:
        (A) LENGTH: 2219 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION:13..1983

(xi) SEQUENCE DESCRIPTION: SEQ ID NO: 3:

```
AATTCCGGAG CC ATG GTG AAC GAA GCC AGA GGA AAC AGC AGC CTC AAC              48
              Met Val Asn Glu Ala Arg Gly Asn Ser Ser Leu Asn
                              665                 670

CCC TGC TTG GAG GGC AGT GCC AGC AGT GGC AGT GAG AGC TCC AAA GAT            96
Pro Cys Leu Glu Gly Ser Ala Ser Ser Gly Ser Glu Ser Ser Lys Asp
            675                 680                 685

AGT TCG AGA TGT TCC ACC CCG GGC CTG GAC CCT GAG CGG CAT GAG AGA           144
Ser Ser Arg Cys Ser Thr Pro Gly Leu Asp Pro Glu Arg His Glu Arg
        690                 695                 700

CTC CGG GAG AAG ATG AGG CGG CGA TTG GAA TCT GGT GAC AAG TGG TTC           192
Leu Arg Glu Lys Met Arg Arg Arg Leu Glu Ser Gly Asp Lys Trp Phe
705                 710                 715                 720

TCC CTG GAA TTC TTC CCT CCT CGA ACT GCT GAG GGA GCT GTC AAT CTC           240
Ser Leu Glu Phe Phe Pro Pro Arg Thr Ala Glu Gly Ala Val Asn Leu
                725                 730                 735

ATC TCA AGG TTT GAC CGG ATG GCA GCA GGT GGC CCC CTC TAC ATA GAC           288
Ile Ser Arg Phe Asp Arg Met Ala Ala Gly Gly Pro Leu Tyr Ile Asp
            740                 745                 750

GTG ACC TGG CAC CCA GCA GGT GAC CCT GGC TCA GAC AAG GAG ACC TCC           336
Val Thr Trp His Pro Ala Gly Asp Pro Gly Ser Asp Lys Glu Thr Ser
        755                 760                 765

TCC ATG ATG ATC GCC AGC ACC GCC GTG AAC TAC TGT GGC CTG GAG ACC           384
Ser Met Met Ile Ala Ser Thr Ala Val Asn Tyr Cys Gly Leu Glu Thr
770                 775                 780
```

-continued

```
ATC CTG CAC ATG ACC TGC TGC CGT CAG CGC CTG GAG GAG ATC ACG GGC      432
Ile Leu His Met Thr Cys Cys Arg Gln Arg Leu Glu Glu Ile Thr Gly
785                 790                 795                 800

CAT CTG CAC AAA GCT AAG CAG CTG GGC CTG AAG AAC ATC ATG GCG CTG      480
His Leu His Lys Ala Lys Gln Leu Gly Leu Lys Asn Ile Met Ala Leu
                    805                 810                 815

CGG GGA GAC CCA ATA GGT GAC CAG TGG GAA GAG GAG GGA GGC TTC          528
Arg Gly Asp Pro Ile Gly Asp Gln Trp Glu Glu Glu Gly Gly Phe
                820                 825                 830

AAC TAC GCA GTG GAC CTG GTG AAG CAC ATC CGA AGT GAG TTT GGT GAC      576
Asn Tyr Ala Val Asp Leu Val Lys His Ile Arg Ser Glu Phe Gly Asp
            835                 840                 845

TAC TTT GAC ATC TGT GTG GCA GGT TAC CCC AAA GGC CAC CCC GAA GCA      624
Tyr Phe Asp Ile Cys Val Ala Gly Tyr Pro Lys Gly His Pro Glu Ala
        850                 855                 860

GGG AGC TTT GAG GCT GAC CTG AAG CAC TTG AAG GAG AAG GTG TCT GCG      672
Gly Ser Phe Glu Ala Asp Leu Lys His Leu Lys Glu Lys Val Ser Ala
865                 870                 875                 880

GGA GCC GAT TTC ATC ATC ACG CAG CTT TTC TTT GAG GCT GAC ACA TTC      720
Gly Ala Asp Phe Ile Ile Thr Gln Leu Phe Phe Glu Ala Asp Thr Phe
                    885                 890                 895

TTC CGC TTT GTG AAG GCA TGC ACC GAC ATG GGC ATC ACT TGC CCC ATC      768
Phe Arg Phe Val Lys Ala Cys Thr Asp Met Gly Ile Thr Cys Pro Ile
                900                 905                 910

GTC CCC GGG ATC TTT CCC ATC CAG GGC TAC CAC TCC CTT CGG CAG CTT      816
Val Pro Gly Ile Phe Pro Ile Gln Gly Tyr His Ser Leu Arg Gln Leu
            915                 920                 925

GTG AAG CTG TCC AAG CTG GAG GTG CCA CAG GAG ATC AAG GAC GTG ATT      864
Val Lys Leu Ser Lys Leu Glu Val Pro Gln Glu Ile Lys Asp Val Ile
        930                 935                 940

GAG CCA ATC AAA GAC AAC GAT GCT GCC ATC CGC AAC TAT GGC ATC GAG      912
Glu Pro Ile Lys Asp Asn Asp Ala Ala Ile Arg Asn Tyr Gly Ile Glu
945                 950                 955                 960

CTG GCC GTG AGC CTG TGC CAG GAG CTT CTG GCC AGT GGC TTG GTG CCA      960
Leu Ala Val Ser Leu Cys Gln Glu Leu Leu Ala Ser Gly Leu Val Pro
                    965                 970                 975

GGC CTC CAC TTC TAC ACC CTC AAC CGC GAG ATG GCT ACC ACA GAG GTG     1008
Gly Leu His Phe Tyr Thr Leu Asn Arg Glu Met Ala Thr Thr Glu Val
                980                 985                 990

CTG AAG CGC CTG GGG ATG TGG ACT GAG GAC CCC AGG CGT CCC CTA CCC     1056
Leu Lys Arg Leu Gly Met Trp Thr Glu Asp Pro Arg Arg Pro Leu Pro
            995                 1000                1005

TGG GCT CTC AGT GCC CAC CCC AAG CGC CGA GAG GAA GAT GTA CGT CCC     1104
Trp Ala Leu Ser Ala His Pro Lys Arg Arg Glu Glu Asp Val Arg Pro
        1010                1015                1020

ATC TTC TGG GCC TCC AGA CCA AAG AGT TAC ATC TAC CGT ACC CAG GAG     1152
Ile Phe Trp Ala Ser Arg Pro Lys Ser Tyr Ile Tyr Arg Thr Gln Glu
1025                1030                1035                1040

TGG GAC GAG TTC CCT AAC GGC CGC TGG GGC AAT TCC TCT TCC CCT GCC     1200
Trp Asp Glu Phe Pro Asn Gly Arg Trp Gly Asn Ser Ser Ser Pro Ala
                    1045                1050                1055

TTT GGG GAG CTG AAG GAC TAC TAC CTC TTC TAC CTG AAG AGC AAG TCC     1248
Phe Gly Glu Leu Lys Asp Tyr Tyr Leu Phe Tyr Leu Lys Ser Lys Ser
                1060                1065                1070

CCC AAG GAG GAG CTG CTG AAG ATG TGG GGG GAG GAG CTG ACC AGT GAA     1296
Pro Lys Glu Glu Leu Leu Lys Met Trp Gly Glu Glu Leu Thr Ser Glu
            1075                1080                1085

GCA AGT GTC TTT GAA GTC TTT GTT CTT TAC CTC TCG GGA GAA CCA AAC     1344
Ala Ser Val Phe Glu Val Phe Val Leu Tyr Leu Ser Gly Glu Pro Asn
        1090                1095                1100
```

```
CGG AAT GGT CAC AAA GTG ACT TGC CTG CCC TGG AAC GAT GAG CCC CTG      1392
Arg Asn Gly His Lys Val Thr Cys Leu Pro Trp Asn Asp Glu Pro Leu
1105                1110                1115                1120

GCG GCT GAG ACC AGC CTG CTG AAG GAG GAG CTG CTG CGG GTG AAC CGC      1440
Ala Ala Glu Thr Ser Leu Leu Lys Glu Glu Leu Leu Arg Val Asn Arg
                1125                1130                1135

CAG GGC ATC CTC ACC ATC AAC TCA CAG CCC AAC ATC AAC GGG AAG CCG      1488
Gln Gly Ile Leu Thr Ile Asn Ser Gln Pro Asn Ile Asn Gly Lys Pro
            1140                1145                1150

TCC TCC GAC CCC ATC GTG GGC TGG GGC CCC AGC GGG GGC TAT GTC TTC      1536
Ser Ser Asp Pro Ile Val Gly Trp Gly Pro Ser Gly Gly Tyr Val Phe
            1155                1160                1165

CAG AAG GCC TAC TTA GAG TTT TTC ACT TCC CGC GAG ACA GCG GAA GCA      1584
Gln Lys Ala Tyr Leu Glu Phe Phe Thr Ser Arg Glu Thr Ala Glu Ala
        1170                1175                1180

CTT CTG CAA GTG CTG AAG AAG TAC GAG CTC CGG GTT AAT TAC CAC CTT      1632
Leu Leu Gln Val Leu Lys Lys Tyr Glu Leu Arg Val Asn Tyr His Leu
1185                1190                1195                1200

GTC AAT GTG AAG GGT GAA AAC ATC ACC AAT GCC CCT GAA CTG CAG CCG      1680
Val Asn Val Lys Gly Glu Asn Ile Thr Asn Ala Pro Glu Leu Gln Pro
                1205                1210                1215

AAT GCT GTC ACT TGG GGC ATC TTC CCT GGG CGA GAG ATC ATC CAG CCC      1728
Asn Ala Val Thr Trp Gly Ile Phe Pro Gly Arg Glu Ile Ile Gln Pro
            1220                1225                1230

ACC GTA GTG GAT CCC GTC AGC TTC ATG TTC TGG AAG GAC GAG GCC TTT      1776
Thr Val Val Asp Pro Val Ser Phe Met Phe Trp Lys Asp Glu Ala Phe
            1235                1240                1245

GCC CTG TGG ATT GAG CGG TGG GGA AAG CTG TAT GAG GAG GAG TCC CCG      1824
Ala Leu Trp Ile Glu Arg Trp Gly Lys Leu Tyr Glu Glu Glu Ser Pro
        1250                1255                1260

TCC CGC ACC ATC ATC CAG TAC ATC CAC GAC AAC TAC TTC CTG GTC AAC      1872
Ser Arg Thr Ile Ile Gln Tyr Ile His Asp Asn Tyr Phe Leu Val Asn
1265                1270                1275                1280

CTG GTG GAC AAT GAC TTC CCA CTG GAC AAC TGC CTC TGG CAG GTG GTG      1920
Leu Val Asp Asn Asp Phe Pro Leu Asp Asn Cys Leu Trp Gln Val Val
                1285                1290                1295

GAA GAC ACA TTG GAG CTT CTC AAC AGG CCC ACC CAG AAT GCG AGA GAA      1968
Glu Asp Thr Leu Glu Leu Leu Asn Arg Pro Thr Gln Asn Ala Arg Glu
            1300                1305                1310

ACG GAG GCT CCA TGA CCCTGCGTCC TGACGCCCTG CGTTGGAGCC ACTCCTGTCC      2023
Thr Glu Ala Pro *
        1315

CGCCTTCCTC CTCCACAGTG CTGCTTCTCT TGGGAACTCC ACTCTCCTTC GTGTCTCTCC    2083

CACCCCGGCC TCCACTCCCC CACCTGACAA TGGCAGCTAG ACTGGAGTGA GGCTTCCAGG    2143

CTCTTCCTGG ACCTGAGTCG GCCCCACATG GGAACCTAGT ACTCTCTGCT CTAAAAAAAA    2203

AAAAAAAAAA GGAATT                                                    2219

(2) INFORMATION FOR SEQ ID NO: 4:

(i) SEQUENCE CHARACTERISTICS:
        (A) LENGTH: 656 amino acids
        (B) TYPE: amino acid
        (D) TOPOLOGY: linear (ii) MOLECULE TYPE: protein (xi) SEQUENCE DESCRIPTION: SEQ ID NO: 4:

Met Val Asn Glu Ala Arg Gly Asn Ser Ser Leu Asn Pro Cys Leu Glu
1               5                   10                  15
```

-continued

```
Gly Ser Ala Ser Ser Gly Ser Glu Ser Ser Lys Asp Ser Ser Arg Cys
            20                  25                  30

Ser Thr Pro Gly Leu Asp Pro Glu Arg His Glu Arg Leu Arg Glu Lys
            35                  40                  45

Met Arg Arg Arg Leu Glu Ser Gly Asp Lys Trp Phe Ser Leu Glu Phe
 50                  55                  60

Phe Pro Pro Arg Thr Ala Glu Gly Ala Val Asn Leu Ile Ser Arg Phe
 65                  70                  75                  80

Asp Arg Met Ala Ala Gly Gly Pro Leu Tyr Ile Asp Val Thr Trp His
                85                  90                  95

Pro Ala Gly Asp Pro Gly Ser Asp Lys Glu Thr Ser Ser Met Met Ile
                100                 105                 110

Ala Ser Thr Ala Val Asn Tyr Cys Gly Leu Glu Thr Ile Leu His Met
            115                 120                 125

Thr Cys Cys Arg Gln Arg Leu Glu Glu Ile Thr Gly His Leu His Lys
            130                 135                 140

Ala Lys Gln Leu Gly Leu Lys Asn Ile Met Ala Leu Arg Gly Asp Pro
145                 150                 155                 160

Ile Gly Asp Gln Trp Glu Glu Glu Gly Gly Phe Asn Tyr Ala Val
                165                 170                 175

Asp Leu Val Lys His Ile Arg Ser Glu Phe Gly Asp Tyr Phe Asp Ile
                180                 185                 190

Cys Val Ala Gly Tyr Pro Lys Gly His Pro Glu Ala Gly Ser Phe Glu
                195                 200                 205

Ala Asp Leu Lys His Leu Lys Glu Lys Val Ser Ala Gly Ala Asp Phe
                210                 215                 220

Ile Ile Thr Gln Leu Phe Phe Glu Ala Asp Thr Phe Phe Arg Phe Val
225                 230                 235                 240

Lys Ala Cys Thr Asp Met Gly Ile Thr Cys Pro Ile Val Pro Gly Ile
                245                 250                 255

Phe Pro Ile Gln Gly Tyr His Ser Leu Arg Gln Leu Val Lys Leu Ser
                260                 265                 270

Lys Leu Glu Val Pro Gln Glu Ile Lys Asp Val Ile Glu Pro Ile Lys
            275                 280                 285

Asp Asn Asp Ala Ala Ile Arg Asn Tyr Gly Ile Glu Leu Ala Val Ser
290                 295                 300

Leu Cys Gln Glu Leu Leu Ala Ser Gly Leu Val Pro Gly Leu His Phe
305                 310                 315                 320

Tyr Thr Leu Asn Arg Glu Met Ala Thr Thr Glu Val Leu Lys Arg Leu
                325                 330                 335

Gly Met Trp Thr Glu Asp Pro Arg Arg Pro Leu Pro Trp Ala Leu Ser
                340                 345                 350

Ala His Pro Lys Arg Arg Glu Glu Asp Val Arg Pro Ile Phe Trp Ala
            355                 360                 365

Ser Arg Pro Lys Ser Tyr Ile Tyr Arg Thr Gln Glu Trp Asp Glu Phe
            370                 375                 380

Pro Asn Gly Arg Trp Gly Asn Ser Ser Ser Pro Ala Phe Gly Glu Leu
385                 390                 395                 400

Lys Asp Tyr Tyr Leu Phe Tyr Leu Lys Ser Lys Ser Pro Lys Glu Glu
                405                 410                 415

Leu Leu Lys Met Trp Gly Glu Leu Thr Ser Glu Ala Ser Val Phe
                420                 425                 430
```

```
Glu Val Phe Val Leu Tyr Leu Ser Gly Glu Pro Asn Arg Asn Gly His
        435                 440                 445

Lys Val Thr Cys Leu Pro Trp Asn Asp Glu Pro Leu Ala Ala Glu Thr
        450                 455                 460

Ser Leu Leu Lys Glu Glu Leu Leu Arg Val Asn Arg Gln Gly Ile Leu
465                 470                 475                 480

Thr Ile Asn Ser Gln Pro Asn Ile Asn Gly Lys Pro Ser Ser Asp Pro
                485                 490                 495

Ile Val Gly Trp Gly Pro Ser Gly Gly Tyr Val Phe Gln Lys Ala Tyr
            500                 505                 510

Leu Glu Phe Phe Thr Ser Arg Glu Thr Ala Glu Ala Leu Leu Gln Val
        515                 520                 525

Leu Lys Lys Tyr Glu Leu Arg Val Asn Tyr His Leu Val Asn Val Lys
        530                 535                 540

Gly Glu Asn Ile Thr Asn Ala Pro Glu Leu Gln Pro Asn Ala Val Thr
545                 550                 555                 560

Trp Gly Ile Phe Pro Gly Arg Glu Ile Ile Gln Pro Thr Val Val Asp
                565                 570                 575

Pro Val Ser Phe Met Phe Trp Lys Asp Glu Ala Phe Ala Leu Trp Ile
            580                 585                 590

Glu Arg Trp Gly Lys Leu Tyr Glu Glu Glu Ser Pro Ser Arg Thr Ile
        595                 600                 605

Ile Gln Tyr Ile His Asp Asn Tyr Phe Leu Val Asn Leu Val Asp Asn
610                 615                 620

Asp Phe Pro Leu Asp Asn Cys Leu Trp Gln Val Val Glu Asp Thr Leu
625                 630                 635                 640

Glu Leu Leu Asn Arg Pro Thr Gln Asn Ala Arg Glu Thr Glu Ala Pro
                645                 650                 655

(2) INFORMATION FOR SEQ ID NO: 5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 5:

AGCCTCAACC CCTGCTTGGA GG                                        22

(2) INFORMATION FOR SEQ ID NO: 6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: YES (xi) SEQUENCE DESCRIPTION: SEQ ID NO: 6:

TGACAGTTTG CTCCCCAGGC AC                                        22
```

(2) INFORMATION FOR SEQ ID NO: 7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 7:

TGAAGGAGAA GGTGTCTGCG GGA                                          23

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: YES (xi) SEQUENCE DESCRIPTION: SEQ ID NO: 8:

AGGACGGTGC GGTGAGAGTG G                                             21

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 9:

CACTGTGGTT GGCATGGATG ATG                                          23

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: YES (xi) SEQUENCE DESCRIPTION: SEQ ID NO: 10:

GGCTGCTCTT GGACCCTCCT C                                             21

(2) INFORMATION FOR SEQ ID NO: 11:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 11:

TGCTTCCGGC TCCCTCTAGC C                                              21

(2) INFORMATION FOR SEQ ID NO: 12:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: YES (xi) SEQUENCE DESCRIPTION: SEQ ID NO: 12:

CCTCCCGCTC CCAAGAACAA AG                                             22

(2) INFORMATION FOR SEQ ID NO: 13:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 13:

TGAAGGAGAA GGTGTCTGCG GGA                                            23

(2) INFORMATION FOR SEQ ID NO: 14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: YES (iv) ANTI-SENSE: NO (xi) SEQUENCE DESCRIPTION: SEQ ID NO: 14:

AGGACGGTGC GGTGAGAGTG                                                20